United States Patent [19]
Winkler et al.

[11] Patent Number: 5,589,329
[45] Date of Patent: Dec. 31, 1996

[54] METHODS AND COMPOSITIONS FOR DETECTING BASE PAIR MISMATCHES

[75] Inventors: Matthew Winkler, Austin; Marianna M. Goldrick, Pflugerville, both of Tex.

[73] Assignee: Ambion, Inc., Austin, Tex.

[21] Appl. No.: 155,937

[22] Filed: Nov. 15, 1993

[51] Int. Cl.[6] .................................................. C12Q 1/68
[52] U.S. Cl. ........................ 435/5; 435/6; 435/91.1; 435/91.2; 435/196; 435/199; 435/810; 436/501; 530/350; 536/23.1; 536/24.1; 536/24.3; 536/24.31; 536/24.32; 536/24.33; 935/78; 935/88
[58] Field of Search .......................... 435/5, 6, 91.1, 435/91.2, 810, 196, 199; 436/501; 536/22.1, 23.1, 24.1, 24.3–.33; 530/350; 935/78, 88

[56] References Cited

U.S. PATENT DOCUMENTS

| | | | |
|---|---|---|---|
| 4,683,202 | 7/1987 | Mullis | 435/91 |
| 4,946,773 | 8/1990 | Maniatis et al. | 435/6 |

OTHER PUBLICATIONS

Gilman, "Ribonuclease Protection Assay", *Current Protocols in Molecular Biology*, Ausubel, F. N. et al., Ed., Unit 4.7:4.7.1–4.7.8, 1987, Mass. Gen. Hosp., Harvard Med. School, Boston, MA.

Dunn et al., "Identification of Germline and Somatic Mutations Affecting the Retinoblastoma Gene", *Science*, 241:1797–1800, 1988.

Friedberg et al., "Selective Detection of mRNA Forms Encoding the Major Phenobarbital Inducible Cytochromes P450 and Other Members of the P45011B Family by the RNAse A Protection Assay", *Archives of Biochemistry and Biophysics*, 279:(1)167–173, 1990.

Genovese et al., "Detection of Mutations in Human Type I Collagen mRNA in Osteogenesis Imperfecta by Indirect RNase Protection", *J. Biol. Chem.*, 264:(16)9632–9637, 1989.

Kain et al., "Universal Promoter for Gene Expression Without Cloning: Expression–PCR", *BioTechniques*, 10:(3)366–373, 1991.

Kim et al., "Occurrence of p53 Gene Abnormalities in Gastric Carcinoma Tumors and Cell Lines", *J. Natl. Cancer Res.*, 83:(13)938–943, 1991.

Kinzler et al., "Identification of a Gene Located at Chromosome 5q21 That is Mutated in Colorectal Cancers", *Science*, 251:1366–1370, 1991.

Krause et al., "[44] Solution Hybridization–Nuclease Protection Assays for Sensitive Detection of Differentially Spliced Substance P–and Neurokinin A–Encoding Messenger Ribonucleic Acids", *Methods in Enzymology*, 168:634–653. (1989).

Myers et al., "Detection of Single Base Substitutions by Ribonuclease Cleavage at Mismatches in RNA:DNA Duplexes", *Science*, 230:1242–1246, 1985.

Myers et al., "Recent Advances in the Development of Methods for Detecting Single–base Substitutions Associated with Human Genetic Diseases", *Cold Spring Harbor Symposia On Quantitative Biology*, LI:275–284. (1986).

Nishisho et al., "Mutations of Chromosome 5q21 Genes in FAP and Colorectal Cancer Patients", *Science*, 253:665–669, 1991.

Perucho, "Detection of Single–base Substitutions with the RNAse A Mismatch Cleavage Method", *Strategies in Molecular Biol.*, 2:(3)37–41, 1989.

(List continued on next page.)

*Primary Examiner*—W. Gary Jones
*Assistant Examiner*—Ardin H. Marschel
*Attorney, Agent, or Firm*—Arnold White & Durkee

[57] ABSTRACT

The present invention discloses improved compositions and methods for detecting mutations, including single base changes, in nucleic acid sequences using RNase protection assays. The improvements include concomitant, dramatic reductions in the salt and RNase enzyme concentrations in the RNase digestion reaction mixture which result in greater sensitivity in detecting genetic mutations. Another embodiment of the present invention is kits to be used for the detection of single base mismatches in nucleic acid samples.

44 Claims, 11 Drawing Sheets

OTHER PUBLICATIONS

Resto et al., "Amplification of Protein Expression in a Cell Free System", *Nucleic Acids Research,* 20:(22)5979–5983, 1992.

Rosenzweig, "Preclinical Diagnosis of Familial Hypertrophic Cardiomyopathy by Genetic Analysis of Blood Lymphocytes", *J. Med. (New England),* 325:(25)1753–1760, 1991.

Sambrook et al., "Molecular Cloning; Mapping Of RNA With Ribonuclease And Radiolabeled RNA Probes", *Cold Spring Harbor Laboratory Press,* 7.71–7.77, 1989.

Sarkar et al., "Access to a Messenger RNA Sequence or Its Protein Product Is Not Limited by Tissue or Species Specificity", *Science,* 244:331–334, 1989.

Stoflet et al., "Genomic Amplification with Transcript Sequencing", *Science,* 239:491–494, 1988.

Storch et al., "RNA Fingerprinting of Respiratory Syncytial Virus Using Ribonuclease Protection", *J. Clin. Invest,* 83:1894–1902, 1989.

Takahashi et al., "p53: A Frequent Target for Genetic Abnormalities in Lung Cancer", *Science,* 246:491–494, 1989.

Ueda et al., "Detection of Multidrug Resistance (MDR1) Gene RNA Expression in Human Tumors by a Sensitive Ribonuclease Protection Assay", *Jpn. J. Cancer Res.,* 80:1127–1132, 1989.

Watkins et al., "Characteristics and Prognostic Implications Of Myosin Missense Mutations In Familial Hypertrophic Cardiomyopathy", *New Engl. J. Med.* 326:(17)1108–1114, 1992.

Winter et al., "A Method to Detect and Characterize Point Mutations in Transcribed Genes: Amplification and Overexpression of the Mutant c–Ki–ras Allele in Human Tumor Cells", *Proc. Natl. Acad. Sci. USA,* 82:7575–7579, 1985.

Gibbs and Caskey, "Identification and Localization of Mutations at the Lesch–Nyhan Locus by Ribonuclease A Cleavage," *Science,* 236:303–305, 1987.

Melton et al., "Efficient in vitro Synthesis of Biologically Active RNA and RNA Hybridization Probes for Plasmids Containing a Bacteriophage SP6 Promoter," *Nucleic Acids Res.,* 12:7035–7056, 1984.

Raines, R. T., "Structure, Mechanism and Function of Ribonucleases," Proceedings of the Second International Meeting, Girona, Spain, Sep. 16–20, 1990, pp. 139–143, Institut de Biologia Fonamental Vicent Villar Palasi, Universitat Autonoma de Barcelona, (Cuchillo et al., eds.), 1991.

Theophilus et al., "Comparison of RNase A, a chemical cleavage and GC–clamped denaturing gradient gel electrophoresis for the detection of mutations in exon 9 of the human acid β–glucosidase gene," *Nucl. Acids Res.,* 17(19):7707–7722, 1989.

Yank and Melera, "Application of the Polymerase Chain Reaction to the Ribonuclease Protection Assay," *BioTechnique,* 13(6):922–927, 1992.

METHODS AND COMPOSITIONS FOR DETECTING BASE PAIR MISMATCHES

The government may own rights in the present invention pursuant to grant number CA57045 from National Institutes of Health.

BACKGROUND OF THE INVENTION

1. Field of the Invention

This invention relates to improved methods for detecting mutations in nucleic acid sequences and, specifically, to the detection of single base change mutations. More particularly, the invention concerns the use of improved reaction conditions, such as concomitantly decreased salt and RNase enzyme concentrations, that allow the detection of many single base mutations which were undetectable in the previously known reaction conditions.

2. Description of the Related Art

Methods for easily and reliably detecting point mutations without prior knowledge of the exact location of the mutations, have wide application in diagnosis and treatment of genetic diseases and cancers, as well as use in genetic counseling. These methods also are of great benefit in the analysis of a variety of human genetic diseases and in establishing human genetic linkage maps.

In many genetic diseases, the causative mutations are scattered over a large number of sites. For example in retinoblastoma, 30% of the cases are the result of widely scattered new mutations (Yandell et al., 1989). In addition, accumulation of point mutations in a variety of genes, such as, for example, p53, ras, and other "protooncogenes" are thought to play fundamental roles in the multi-step process of transformation of normal cells to the malignant state. The ability to detect these mutations is important both for genetic counseling and for early clinical intervention. Improved efficiency and reliability in methods of detecting point mutations should lead to a better understanding of the mechanisms of carcinogenesis and to improved treatment and prognosis for a variety of cancers. The ideal screening method would quickly, inexpensively, and reliably detect all types of widely dispersed point mutations, insertions/deletions, and translocations in genomic DNA, cDNA, or RNA samples depending on the specific situation. Currently there are no methods which achieve these goals.

Over the past ten years, a number of different methods have been used to detect single-base mutations. These methods include denaturing gradient gel electrophoresis, restriction enzyme polymorphism analysis, chemical mismatch methods and others (see Cotton, 1989, for a review of single-base mutation detection methods). Recently, SSCP (single-strand conformation polymorphism) analysis and the closely related heteroduplex analysis methods have come into use for screening for single-base mutations (Orita et al., 1989; Keen et al., 1991). In these methods, the mobility of PCR-amplified test DNA from clinical specimens is compared with the mobility of DNA amplified from normal sources by direct electrophoresis of samples in adjacent lanes of native polyacrylamide or other types of matrix gels. Single-base mutations often alter the secondary structure of the molecule sufficiently to cause slight mobility differences between the normal and mutant PCR products after prolonged electrophoresis.

Unfortunately, SSCP has several major drawbacks. The most important is that not all mutations result in detectable shifts in mobility. Recently it was found that of 20 mutations detected by direct sequencing, only 35% were detected by SSCP (Sarkar et al., 1992). Other studies have reported higher detection efficiencies, but it is clear that SSCP has a major problem in missing point mutations. Chances of detecting mobility differences can be increased by running parallel gels under different conditions, for example at 4° C. and 30° C., with and without 5% glycerol, (Hayashi, 1991), but this significantly increases the cost and labor associated with analysis. Since mobility differences are generally quite small, analysis of genes in the heterozygous state is compromised. Another drawback of SSCP and related techniques is that they provide no information on the position of the mutation within the DNA fragment being analyzed. Also, the time required for SSCP-type analysis is fairly long, since electrophoresis often requires 12–24 hours to resolve the fragments. Furthermore, there seems to be an upper size limit for analysis by SSCP of approximately 300 bases and increased fragment length has been associated with decreased efficiency of mutation detection (Hayashi, 1991).

Direct sequencing of PCR products is often considered to be the most reliable method of identifying unknown mutations. However, the labor and time involved in direct sequencing are extensive. In fact, direct sequencing is the most time consuming step in the identification of point mutations even with the availability of automated sequencing methods. Further, even DNA sequencing may not give a clear indication of a single-base mutation when an individual is heterozygous for that allele. The ambiguity arises because the resulting co-incident bands at the relevant position on the sequencing ladder (Cheng and Haas, 1992) could be mistaken for the ubiquitous artifact of "shadow bands", which are caused by premature termination during the extension reaction. Therefore, the development of reliable, preliminary screening methods to eliminate the unnecessary sequencing of DNA fragments which do not contain mutations is an immediate need in the art.

Ribonuclease protection assay (RPA) is another technique used for detection of dispersed single-base mutations. In this procedure, a labeled antisense RNA probe is hybridized to a complementary test RNA or DNA in solution, and then the remaining unhybridized, single-stranded probe is degraded by ribonuclease treatment. The hybridized, double stranded probe is protected from RNAse digestion. After an appropriate time, the products of the digestion reaction are recovered and analyzed on a gel. If there is a single-base mismatch between the complementary probe and the test nucleic acids, the ribonuclease may cleave the probe at that position, resulting in the appearance of two new bands on the gel (Winter et al., 1985; Myers et al., 1985; Perucho, 1989). The size of these protected fragments gives information regarding the location of the mutation. RPAs have been used to detect single-base mismatches in many different genes, including p53, ras, myc, retinoblastoma, APC, HIV reverse transcriptase, β globin and others (Takahashi, et al., 1989; Forrester et al., 1987; Richman and Hayday, 1989; Dunn et al., 1988; Lopez-Galindez et al., 1991; Myers et al., 1985; Winter et al., 1985).

Historically, RPAs have been successful in detecting about half of all point mutations, provided the analysis is performed on both strands of the test DNA (Myers and Maniatis, 1986; Kinzler et al., 1991). However, some detectable mismatches are only partially cleaved, which decreases the sensitivity of the technique and complicates analysis of heterozygous mutations. The ability to detect all point mutations would greatly increase the utility of this technique and enable it to be applied in clinical settings where a greater than 50% detection rate is necessary.

SUMMARY OF THE INVENTION

The present invention seeks to overcome these and other drawbacks inherent in the prior art by providing methods and compositions to improve the detection of mutations using RNase protection assays. The invention embodies new and improved reaction mixtures for use in detecting base pair mismatches between DNA or RNA samples and RNA probes. These improved reaction conditions were found to surprisingly allow the detection of almost all single base mismatches and mutations. In particular, the invention concerns methods and reaction mixtures with concomitantly reduced salt and Rnase concentrations. In certain aspects, the invention also concerns the use of distinct RNase enzymes and the use of PCR in conjunction with the improved reaction mixtures.

RNase protection assays are generally based upon obtaining a single stranded DNA or RNA test sample and a single stranded DNA or RNA control; mixing the test sample and control separately with a single stranded RNA probe so that the complementary single strands anneal, or hybridize, thereby forming a test sample duplex and a control duplex; treating both duplexes with an RNase enzyme; separating the products of the RNase treatment according to size, and comparing the separated products from the test sample and control duplexes. The 'test sample' is the nucleic acid or amplified product of the said nucleic acid which one wishes to analyze, such as a sample suspected of containing a mutation, whereas the 'control' species will be a DNA or RNA molecule which is known to hybridize, without mismatches, to the single stranded RNA probe employed. The control duplex formed, with no mismatches, will not be substantially cleaved by RNase and will remain primarily as a single fragment. For example, the cleavage of a perfectly matched control and probe will be less than about 10%. However, if the 'test sample duplex' formed contains one or more mismatches it will be cut near the point of the mismatch by RNase, which preferentially cleaves single-stranded RNA, and the test sample nucleic acid will thus be split into two or more smaller sized fragments which may be identified based on size following separation.

It is understood that the test sample nucleic acid and the control nucleic acid may be from a single stranded or a double stranded source. For example, mRNA will be generally single stranded when isolated from a cell and DNA will generally be double stranded when isolated. What is important in the practice of the present invention, however, is that the test sample and the control be made single stranded by, preferably incubation at high temperature before the annealing step is allowed to take place. The high temperature incubation melts apart double stranded nucleic acid molecules and also melts apart regions of double strandedness caused by self-complementarity within the probe and/or the test sample molecule.

Within the scope of the present disclosure, 'contacting a single stranded RNA probe with a control nucleic acid or a test nucleic acid' is understood to mean preparing a solution comprising said probe and nucleic acid and incubating said solution under conditions effective for hybridization of complementary nucleic acid molecules. Variable parameters for said incubation include temperature, time, salt concentration and formamide concentration. Hybridization is understood to mean the formation of stable, anti-parallel duplex molecules based on the specific hydrogen bonding of complementary nucleotide bases of the nucleic acid molecules.

In the most general sense, the present invention concerns the use of reduced salt and low enzyme concentrations in RNase protection assays, such as generally described above. "Reduced salt and low enzyme concentration" is used herein to indicate significantly less salt and RNase enzyme than the routinely employed 300 mM NaCl and 40 µg/ml RNase of the prior art, such as salt concentrations reduced by about 3, 4, 6, 30, or preferably, about 100-fold, and RNase concentrations reduced by about 2,000, 4,000, or preferably, about 13,000-fold. More particularly, the invention provides a method for conducting an RNase protection assay using a reaction mixture which comprises a final salt concentration of between about 15 mM and about 100 mM and a final RNase A enzyme concentration of between about 0.1 ng/ml and about 4000 ng/ml, or between about 0.5 ng/ml and about 1000 ng/ml, or between about 1 ng/ml and about 100 ng/ml and most preferably, of between about 1 ng/ml and about 50 ng/ml.

The use of significantly reduced salt concentrations of between about 3 mM and about 75 mM is contemplated in certain embodiments, with concentrations of between about 3 mM and about 50 mM being particularly preferred, and concentrations of between about 15 mM and about 30 mM being even more preferred, especially where the RNase enzyme is RNase A, modified RNase A, or a mixture of RNase A and RNase B—as is most commonly used. Where the RNase employed is RNase I from $E.\ coli$, it is contemplated that the optimum salt concentration will generally be between about 75 mM and about 100 mM, which is still significantly below the 300 mM taught in the art as exemplified by, e.g., Sambrook et al. (1989) and Winter et al. (1985). As was established by the present inventors, the salt concentration affects the activity of the RNase enzyme, and it is understood that an amount of RNase I or other RNase to be used is that amount which has the same activity as the RNase A in the particular salt concentrations to be used. In preferred embodiments, the salt employed will be sodium chloride (NaCl), although many salts may be adapted for use, such as, for example, LiCl, Na-acetate, $MgCl_2$, KCl or even $MgSO_4$ or $CaCl_2$.

A note of explanation is needed where the salt concentration is concerned. Historically, in the reporting of methods of practicing RPAs, the reported salt concentrations indicate only the amount of salt added after the hybridization step is complete. These reported salt concentrations do not take into account the salt carried over from the hybridization buffer (See for example, U.S. Pat. No. 4,946,773, incorporated herein by reference). For example, hybridization buffer comprising 80% formamide, 300 mM Na-acetate pH 6.4, 100 mM Na-citrate pH 6.4, 1 mM EDTA may be diluted 20-fold into the reaction buffer. In this instance, the reaction solution will contain about 20 mM $Na^+$ before any salt is added into the RNase digestion reaction mix. This is of little concern at the high salt concentrations which have been taught in the past, but at the low salt concentrations of the present invention, the salt carried over from the hybridization reaction becomes significant. Therefore, in the reported salt concentrations of the present disclosure, it is important to understand that these concentrations do not include the carry over from the hybridization reaction. For example, it should be assumed that up to 20 mM salt or cations is carried over into the reaction mix from the hybridization reaction.

Although the present inventors found RNase A to be the most preferred enzyme currently available, the use of other types of RNase enzymes is contemplated so long as they cleave single-stranded RNA preferentially. Or in other words, the enzyme, on encountering a DNA-RNA or RNA-RNA duplex will cleave the RNA molecule in a region of non-hybridized, or single stranded RNA with a 5 fold or even 100 fold higher efficiency than it will cleave the RNA in an area of a double stranded nucleic acid duplex. The single strandedness may be, for example an overhanging end, the loop of a "stem-loop" structure, or the result of a deletion, insertion or rearrangement in either or both of the nucleic acid molecules in the duplex, or it may be the result of a single base pair mismatch.

As used herein, the term "RNase A" is used to encompass purified pancreatic RNase A or derivatives thereof from any organism or source; modified and engineered RNase A forms, such as described by Raines (1991); and also to cover commercially available RNase A, such as that sold by Sigma Chemical Company (Catalog No. R-5125), which is known to be a mixture of RNase A and the differently-glycosylated, RNase B. Other RNase enzyme compositions envisioned to be useful are those comprising RNase I, RNase T2 and RNase P1. The inventors have discovered that RNase I is able to specifically cleave and A/C mismatch, and that the cleavage was more complete in low salt/enzyme conditions than in the presence of high salt/enzyme concentrations. Other enzymes which are contemplated to be useful in the method of the present invention are barnase, the extracellular ribonucleases from *Bacillus intermedius, Streptomyces erythraeus* and *Ustilago sphaerogena,* and the single strand specific nucleases such as S1 and mung bean nuclease, or even compositions comprising a combination of any of such enzymes. In preliminary tests, mung bean nuclease has been found to cleave an A/C mismatch at approximately 10% at an enzyme concentration of 0.015 u/µl in a buffer containing 10 mM NaCl. Given the concept of concomitantly reduced salt and RNase solutions embodied in the present invention, defining the optimal salt and enzyme concentration ranges for a particular RNase enzyme with a particular probe will be a straightforward matter for those of skill in the art in light of the present disclosure.

Although the present inventors found reduced salt and RNase concentration to maximize cleavage at single base mismatches, other reaction conditions can be envisioned which would increase the effectiveness of this technique. In a general sense, these would include agents which are consistent with hybridization of two complementary strands of nucleic acid, but which act to increase the deformation of the nucleic acid duplex at single base mismatches rendering the duplex more susceptible to cleavage by RNase at or near the mismatch. Such agents might include intercalating agents such as ethidium bromide which preferentially bind double stranded nucleic acids over single stranded nucleic acids. Reaction temperature, pH, formamide, or other denaturants or silver or other metal ions may also favor preferential cleavage at single base mismatches. It is also understood that use of the term "single base mismatches" also encompasses larger mismatches such as those caused by single base or larger insertions or deletions or double base or larger mismatches.

In a preferred embodiment of the invention, the products of RNase treatment are separated by a gel electrophoresis method, such as polyacrylamide or agarose gel electrophoresis. Subjecting the products of the RNase cleavage reaction to gel electrophoresis through the appropriate gel matrix will reveal differences in the sizes of the products of the RNase digestion of the test sample vs. the control duplex. For instance, by including size standard fragments of DNA or RNA in one or more lanes of the gel, the size of the fragments generated by the RNase cleavage reaction can be estimated. By way of example, if a probe of 1000 bases is used, and the gel indicates products of 200 and 800 bases, it can be determined that a single mutation exists in the test sample 200 bases from one end of the probe. A larger number of fragments in the products would mean that more than one mutation is present.

Preferably, the single stranded RNA probe will be labelled either with a radioactive isotope or non-radioactively, for example, with biotin. The RNA probe may be synthesized by any method known to those of skill in the art, such as, e.g., transcription from plasmid or viral vectors, or transcription from amplified products using phage promoters (Innis et al., 1990; Sambrook et al., 1989). Synthesis from an SP6, T7 or T3 bacteriophage promoters (Melton, 1984) is considered to be particularly useful, as are the methods disclosed in U.S. application Ser. No. 07/810,968, incorporated herein by reference.

The test sample and probe may be between 0.05 kb and 10 kb in size and would more preferably be between 0.75 and 3 kb, and most preferably between about 100 and 2,000 bases, although almost any sized species may be employed if desired. The single stranded DNA or RNA test sample employed may be derived from genomic DNA, cDNA, or derived from somatic cells, mitochondria, chloroplasts, or from inserts from various vectors such as plasmids, cosmids, phage, YACs and the like. The RNA test sample may also be transcribed from any of these sources. In addition, the sample may be derived from endogenous mRNA by reverse transcriptase PCR. The test sample may also be synthesized by automated synthesis or the like. The test sample may also be derived from an RNA species such as mRNA, tRNA, rRNA or others from any species and may be first converted to DNA by reverse transcriptase and then amplified and transcribed. A particularly advantageous method is contemplated to be that using the polymerase chain reaction (PCR) method, as described in U.S. Pat. No. 4,683,202, incorporated herein by reference. The PCR amplification of the products is particularly useful as these products can then be produced in sufficient quantities that they can be visualized by ethidium bromide staining, for example, so that the use of radioactive labelling is not necessary.

The improved RNase cleavage procedure disclosed herein provides a sensitive and reliable means of detecting mutations, particularly including single base substitutions, and also small deletions or insertions, in endogenous DNA or RNA, or in DNA amplified from endogenous sources by PCR, or in RNA transcribed from DNA amplified by PCR. The innovation described in the present disclosure allows the detection of close to 100% of such mutations rather than the 50–75% that were detectable with the methods now in use. In addition, analysis of the sizes of the RNase cleavage products of the RNA:DNA or RNA:RNA duplexes not only provides evidence for the presence of a single base mismatch in the experimental sample RNA or DNA, but it also makes it possible to localize the mismatch to within about 10% or better of the fragment size depending on the resolution of the separation system used to analyze the size of the fragments. The present invention also encompasses methods for detecting other mutations, such as small deletions and insertions which are readily detectable using the compositions and methods disclosed herein. Naturally, the terminology employed with respect to 'test sample' and 'control' molecules may be reversed and 'controls' with a known mutation could be employed to search for other segments of DNA or RNA with such mutations, such as in the members of a family of which one member is known to carry a particular heritable genetic mutation.

The improved RNase A cleavage procedure of the present invention will be applicable to a variety of problems where the detection and localization of single base substitutions is important. For example, the procedure can be applied to the analysis of human genetic diseases and for screening DNA for genetic counseling. This method can also be used to detect and analyze genetic mutations associated with many human cancers, such as, for example, mutations in p53, ras, neu, myc, abl, and to screen for cancer- or disease-associated mutations in these or any other genes, including HIV reverse transcriptase and β globin as well as mutations in agricultural products.

An inherent advantage of this procedure is the localization of mutations. Often, mutations are known to exist in an organism based on phenotypic expression, but the location of the mutation is not known. The RNase screening procedure can be used to rapidly screen large numbers of cloned DNA fragments to localize the mutation to a smaller region of DNA, for example in testing variants of the Human Immunodeficiency Virus (HIV) which have become immune to host defenses in AIDS. Other applications include, but are not limited to viral typing and long range genetic mapping in order to understand genetic evolution of particular genes.

In further embodiments, the present invention concerns kits for use in conducting RNase protection assays. Such kits will generally comprise a reduced salt concentration solution, low enzyme concentration reaction mixture in accordance with the present invention, or a mixture which, when admixed, diluted or brought into solution will provide such a reaction mixture. It is contemplated that the kits will also provide a double stranded control nucleic acid molecule and control probes, (or templates to make such probes) designed to hybridize to both strands of the control sample with no mismatches.

Of course it is understood that in addition to the clinical and genetic counseling applications of the present invention, the invention will be useful in a wide variety of situations. Rapid, economical screening of any type of point mutations or small deletions or insertions that are generated in a laboratory, and that can be expressed as a DNA molecule or an RNA transcript will be a welcome addition to the art of genetic research as it is now practiced. This includes the study of the contribution of individual amino acids to protein folding and structure as well as enzymatic mechanisms. Other uses include, but are not limited to the study of mutations and how they are related to phenotypic changes in any number of organisms. The determination of genetic "family trees" will also benefit from the present invention as mutations can be localized without sequencing the entire genes of the various organisms. These and many other applications will be obvious to those of skill in the art and are encompassed within the present invention.

DESCRIPTION OF THE PREFERRED EMBODIMENTS

A. Introduction

Figure 1:
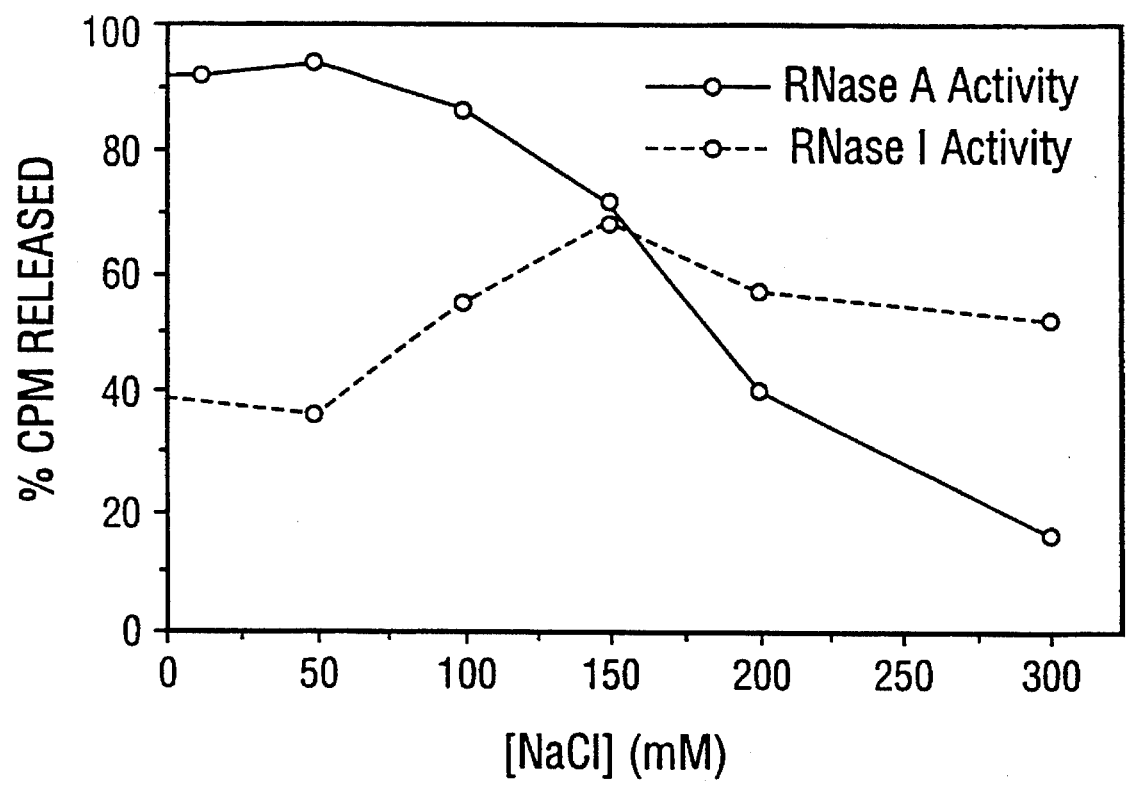
FIG. 1 represents the effect of NaCl concentration on the activity of RNase A and RNase I. Activity levels of both enzymes are reported as % CPM of $^{32}$P-labelled single stranded RNA released by RNase digestion at various NaCl concentrations.

RNase Protection Analysis or RNase Protection Assay (RPA) is a general procedure for detecting and quantifying RNA (usually mRNA expressed in a given tissue or cell type). The RPA technique has also been applied to the detection of dispersed single base mutations. In the general procedure, a labeled (usually radiolabeled) RNA transcript which is complementary to a test sample mRNA or DNA being analyzed for mutation is synthesized in vitro. The labeled RNA is referred to as the probe. Probe and test sample nucleic acids are mixed, heated to temperatures sufficient to denature their secondary structure, and then cooled to permit complementary probe and test sample sequences to base-pair or hybridize. The hybridized nucleic acid mixture is then treated with ribonuclease, RNase A for example. This treatment degrades all remaining single-stranded, unhybridized probe, while the portion of the probe which is hybridized to its complementary test sample nucleic acid is resistant to, or protected from RNase degradation. The protected, labeled probe is then recovered and analyzed, preferably by polyacrylamide gel electrophoresis and autoradiography. If there is an unpaired base or a mismatch between the probe and test sample nucleic acids (which could result, for example, from a point mutation in the test sample nucleic acid) the RNase is sometimes able to cleave the probe at that position, resulting in an alteration in the size and thus the mobility of the protected products on the gel. The size of the protected fragments provides information on the location of the mutation. The ability of the RNase to recognize and cleave a probe at a mismatch depends on the concentration of RNase and on the reaction conditions chosen, for example the composition of the mixture used for RNase digestion. The reaction conditions not only influence the activity of the enzyme, but also have a critical effect on the nature of the substrate, i.e., the hybridized probe-test sample nucleic acids.

The tendency for two complementary strands of nucleic acid in solution to anneal or hybridize by forming hydrogen bonds between their complementary bases, is critically dependent on the concentration of monovalent or divalent cations in the solution. Sodium ($Na^+$), has been the cation of choice for determining the effects of salt concentration on the stability of duplex nucleic acids. Above a threshold $Na^+$ concentration, two complementary single strands (either DNA or RNA) of nucleic acid will hydrogen bond through interaction of the bases in each strand, to form a double-stranded molecule of DNA, RNA, or even a DNA-RNA heteroduplex. Complementary bases are adenosine and thymidine (in DNA), or adenosine and uridine (in RNA), and cytosine and guanine in both DNA and RNA. Two hydrogen bonds are formed between paired A and T or A and U residues, while C-G base pairing results in the formation of three hydrogen bonds. The G-C base pair is therefore a stronger interaction than the A-U or A-T base pair. In general, hydrogen bonding (leading to duplex formation) does not occur between non-complementary bases. The ability of two single strands to form a stable double-stranded duplex depends on the sequence of bases in each strand being complementary to the other, such that when the strands are aligned in an antiparallel orientation, sequential juxtaposed bases are able to form hydrogen bonds. Although hydrogen bonding between any two complementary bases provides only a weak binding energy, the cumulative binding energy between many sequential paired bases provides sufficient attractive forces to hold the strands together in a stable duplex. Cations enhance the tendency for complementary strands to form hydrogen bonds, by masking the negative charges of the phosphate groups in the phosphodiester linkages which form the "backbone" of the nucleic acid strands. At low concentrations of positively charged ions, repulsive forces between negatively charged strands favor their single-stranded or denatured conformation; as cation concentration is raised, the negative charges are masked, complementary bases pair through hydrogen bonding, and a duplex nucleic acid molecule is formed. In a duplex containing a mismatched (non-complementary) base pair, the single unpaired position in the two otherwise complementary strands provides the target for the single-strand specific RNase in the RNase protection assay.

Other parameters besides cation concentration affect the tendency of complementary strands to exist in the alternative double-stranded or single-stranded conformations. Temperature is a critical variable; as the temperature of a solution of duplex nucleic acid molecules is raised, hydrogen bonds are broken first in A-U rich regions and finally in G-C rich regions, until above a critical temperature, the complementary strands come apart. The composition of the two strands, i.e., their % GC content, determines the critical temperature for duplex denaturation at a given ionic strength. As a corollary, the % GC also determines the threshold concentration of $Na^+$ needed to maintain duplex stability at a given temperature. Stability of duplex nucleic acid molecules in solution is also affected by the nature of the solvent. For example, duplexes are much less stable in formamide (which destabilizes hydrogen bonds) than in aqueous solution, a fact exploited by molecular biologists to achieve nucleic acid hybridization at lower temperatures than would otherwise be required.

Equations have been derived to relate duplex formation to the major variables of temperature, salt concentration, nucleic acid strand length and composition, and formamide concentration.
Eg:

1. $Tm = 81.5 - 16.6(\log[Na^+]) + 0.41(\% \, GC) - 600/N$ (Tm=temperature for duplex to half denature; N=chain length 2. $Tm = 81.5 - 16.6(\log[Na^+]) + 0.41(\% \, GC) - 0.63(\% \, formamide) - 600/N$ One can thus predict whether complementary strands will exist in double-stranded or single-stranded form under a given set of conditions. If conditions are chosen such that complementary strands form a stable duplex, the duplex will in theory be resistant to the nucleolytic action of enzymes (DNases and RNases) which are specific for cleavage of phosphodiester bonds in single-stranded molecules. Many different types of nucleases exist, which vary widely in their substrate specificities. The RNases commonly used in RNase protection assays are specific for cleavage after particular bases in single-stranded RNA molecules. Below the threshold $Na^+$ concentration needed to maintain duplex stability, the complementary RNA strands denature into single strands, which are then substrates for degradation by the RNases. Susceptibility to digestion by RNase A is therefore a functional assay for whether complementary strands exist as single-stranded or double-stranded molecules.

A major embodiment of the present invention is the surprising discovery that the concentration of RNase A is also a critical variable in determining whether two RNA strands form a stable duplex, as defined by resistance to digestion by RNase A. This is particularly true at salt concentrations which are close to the minimum required for duplex stability. Historically, RNase A digestions have been carried out at high concentrations of NaCl, usually 300 mM for example (Myers and Maniatis, 1986), although as low as 100 mM in one case (Genovese et al., 1989). RNase A concentrations required for mismatch-specific cleavage at said high NaCl concentrations are typically 40 µg/ml (Sambrook et al., 1989; Winter et al., 1985) or less commonly 5 µg/ml (Dunn et al., 1988), 10 µg/ml (Storch et al., 1989) or 30 µg/ml (Perucho, 1989).

A surprising and unexpected discovery of the present invention is that most of the mismatches tested were not efficiently cleaved under the conditions taught in the art, but that mismatch cleavage by RNase was achieved when the NaCl concentration was reduced to 3–10 mM. However, simply reducing the NaCl concentration in the presence of standard RNase levels, resulted in complete degradation of both perfectly base-paired and mismatch-containing RNA duplexes. Only by dramatic reduction of the RNase concentration, in conjunction with the reduced NaCl concentration, was the necessary specificity of cleavage maintained. In other words, the RNA duplex containing the single-base mismatch was cleaved, while the perfectly base-paired control duplex remained relatively resistant to cleavage. Reducing the RNase concentration by about 4,000 to 13,000-fold over levels used in the usual practice of the art permitted specific mismatch cleavage by RNase.

RNase protection assays have been used to detect single-base mismatches in various genes, including p53, ras, myc, retinoblastoma, APC, HIV reverse transcriptase and β globin (Takahashi, et al., 1989; Forrester et al., 1987; Richman and Hayday, 1989; Dunn et al., 1988; Lopez-Galindez et al., 1991; Myers et al., 1985; Winter et al., 1985). However, these techniques can generally only detect about half of all point mutations, even when the analysis is performed on both strands of the test sample DNA (Myers and Maniatis, 1986; Kinzler et al., 1991). Clearly, modification to this technique directed to improving the point mutation detection frequency represents a significant advance in the field.

Another difficulty in detecting genetic diseases is the presence of a normal allele in the case of a heterozygous defect. If the mutant allele in question has been cloned, performing the cleavage reaction with RNA probes complementary to this allele would overcome the uncertainty of heterozygosity since the presence of a wild type allele should then be detected in the cleavage products. This approach is especially valuable in the diagnosis of human genetic diseases; in fact, the use of both wild type and mutant oligonucleotide probes is an obligatory requirement of prenatal diagnosis tests in the method of Orkin et al. (1983).

The present invention embodies, firstly, concomitant re-optimization of both the salt concentration and the RNase concentration which, in combination, have been found to allow the detection of almost all single base mutations. Secondly, the invention includes the concept of using RNase enzymes other than RNase A, such as, for example, RNase I, RNase T2, RNase P1 or a combination of such enzymes. Thirdly, the invention concerns the combination of PCR technology and the improved RPA reaction conditions of the present disclosure to generate sample nucleic acid for subsequent mismatch analysis.

B. Optimization of Reaction Conditions

Historically, reaction conditions for RNase protection have included the presence of relatively high levels of salt and relatively high concentrations of RNase A. Prior to the present invention, the practice taught in the art was to use the following conditions for mismatch cleavage: 40 µg/ml RNase A in 300 mM NaCl, or less commonly, in 200 mM NaCl/100 mM LiCl (Myers et al., 1985; Winter et al., 1985; Takahashi et al., 1989; Sambrook et al., 1989). In some cases, the salt concentration has been lowered and the temperature increased in order to achieve greater sensitivity of the reaction (Genovese, et al., 1989), or lower concentrations of RNase have been used (Dunn, et al., 1988, Storch, et al., 1989). However, there has been no attempt in the past to improve the detection of point mutations by significantly decreasing the salt and enzyme concentrations concurrently in the reaction mix.

The optimization of reaction conditions for RNase protection assays are a major part of the present discovery. The inventors have found that a reduction in salt concentration, combined with a reduction in RNase concentration, results in surprisingly efficient mismatch detection. Significant reductions in NaCl and RNase A concentrations were found to increase the cleavage of most mismatches from undetectable, or barely detectable, levels to virtually complete cleavage (note, A:C was cleaved efficiently under all conditions). The improved reaction conditions of the present discovery comprise significantly lower salt and RNase concentrations, such as, in the order of 3–12 ng/ml RNase A in 3–10 mM NaCl. This represents a 4,000 to 13,000-fold reduction in RNase A concentration, and a 30 to 100-fold reduction in NaCl concentration, over the "50% detection rate" reaction conditions of the prior art.

C. Ribonucleases

There is a large literature describing different ribonucleases, a number of which are commercially available. Enzymes such as RNase T2 from yeasts such as Aspergillus, and RNase P1 (from *Penicillium citrinum*) may also exhibit single-base mismatch cleavage properties and would be included in the scope of the present invention.

In general, any single-stranded ribonuclease enzyme which is capable of cleaving single stranded RNA, and can thus recognize a single base pair mismatch, is considered to be suitable for use in the present invention. The efforts of the inventors has been focused on RNase A, which is a well studied enzyme, and on RNase I from *E. coli*, which has only recently been cloned and over-expressed. It was contemplated that RNase I might be a superior enzyme for single-base mismatch detection, however RNase A is currently believed to be better suited to this purpose.

RNase A is the preferred enzyme due to its better intrinsic mismatch detection ability and a wider dynamic range of enzyme to substrate ratios over which it can effectively detect single-base mismatches. However, RNase I appears to have a better specificity for single stranded vs. double stranded RNA over a wider range of salt concentrations. In addition, its ability to cleave after all four nucleotides (as opposed to RNase A, which is thought to cleave only after pyrimidines), is potentially a major advantage. It seems likely that there exist ribonucleases which will combine the advantages of both enzymes or maybe even have better properties than either enzyme, but RNase A is currently the preferred enzyme.

RNase A

RNase A is found in many organs in vertebrates, but is present in concentrated form in the pancreas. RNase A-like enzymes from a large number of mammalian species (sheep, pig, rat, horse, kangaroo, human, and others) have been isolated and characterized. The many scattered amino acid substitutions found in the different RNases suggest that the enzymes may have different properties and cleavage specificities. Because of its extraordinary ability to renature after boiling, it is likely that RNase A of sufficient purity can be obtained by utilizing a single ammonium sulfate cut followed by boiling to irreversibly denature nonspecific contaminating nucleases. RNase A may be obtained from the pancreas of several different animals, and tested for use in mismatch detection assays.

In certain embodiments, it is contemplated that commercially available RNase A will be preferred for use with the present invention. RNase A may be easily obtained from commercial sources, for example, from Sigma Chemical Company (Catalog No. R-5125). However, it is well known in the art that such commercially available "RNase A" is, in fact, often a combination of RNase A and RNase B, which represent differently glycosylated forms of the enzyme, and thus the use of an RNase A and B mixture is contemplated. Alternatively, RNase A which is essentially free of RNase B, for example, that which is available from Sigma (Catalog No. R-5250) may be used. RNase B (Sigma Catalog No. R-5875) is also encompassed in the scope of the present invention. The RNase A preparation may generally be dissolved in distilled water at a concentration of about 2 mg/ml, placed at 100° C. for 10 minutes, slowly cooled to room temperature and then stored at 4° C. for upwards of one year.

In addition, RNase A mutants may be generated by in vitro mutagenesis and over-expression in *E. coli*. Mutagenesis can be accomplished by standard methods such as site directed mutagenesis. Some existing mutants which are presently available appear to have a much increased ability to cleave at purine residues (Raines, 1991). Thus, they may have desirable characteristics of both RNase A and RNase I and may be very useful in the embodiment of the present invention.

Under the conditions for the RPA reaction as taught in the literature, an A:C mismatched pair is cleaved efficiently, but the other possible mismatch pairs are cleaved less efficiently or not at all. Thus, a success rate of only about 50% to 75% was found to be achievable. However, under the improved method of the present invention, cleavage of all or nearly all single-base mismatches in RNA/RNA duplexes is achievable. Furthermore, using the RNA-RNA reciprocal probe/ test sample strategy where both strands of the mutant are probed, confirming data from detection of the reciprocal mismatches is obtained. This increased efficiency is due to the inventors' discovery that by decreasing the NaCl concentration and the enzyme concentration simultaneously, all mismatch combinations can be detected (except possibly the rare A:A or U:U mismatch which has not been tested completely under the improved method at the time of this disclosure.)

RNase I

RNase I is found in the periplasmic space of *E. coli*. It is likely that enzymes similar to RNase I will be found in other bacterial species localized in the periplasmic space. Partially purified RNase I like enzymes may be obtained from gram negative *halophiles,* such as *Halobacterium salinarium* and *psychrophiles* such as *Colwellia psychroerythrus* and others.

D. Methods for Use in Connection with RNase Protection Assays

RNA Probes

Generally, RNA probes may be derived by in vitro transcription from any cloned and/or PCR amplified fragment of DNA. The region of DNA used to make the probe includes the region of the gene in which it is desired to test for the presence of mutation, and such probes are generally transcribed from wild type templates containing the region of DNA in non-mutated form. The transcripts are generally required to be relatively homogenous in length. Suitable probes may be synthesized in vitro from linearized plasmid DNA clones using standard procedures. The preferred method of synthesizing the probes is using the phage promoter polymerase systems, SP6, T3 and T7, although RNA synthesized from other promoters using different vectors is equally suitable. RNA probes can also be synthesized from DNA fragments amplified by PCR, which have been engineered to contain phage promoter sequences.

Although the RNA probe need not be labelled, it is preferable to do so. One method, called internal labeling, involves the synthesis of radioactively labeled RNA by incorporation of radioactivity labeled nucleotide(s) during the in vitro transcription reaction. In addition to radiolabeled nucleotides, nucleotides labeled by other means such as biotinylation can be used to synthesize internally labeled RNA probes. Alternatively, the RNA probe may be end-labeled after its synthesis either radioactively (e.g. by using polynucleotide kinase) or non-radioactively by chemical means. Because of its greater sensitivity and convenience, internally labeled probes are generally used in the preferred practice.

In an alternate strategy, both complementary strands of the test sample DNA of interest and of the wild type probe can be amplified, generally by PCR. Phage promoters can be added to the opposite ends of the amplified DNA, either by including the phage promoter sequences in the PCR primers, by adding the promoters with a second pair of primers in a separate amplification, or by using primers that flank the promoters in a plasmid clone containing the DNA of interest. The promoters could also be added enzymatically after the PCR amplification, for example with DNA ligase. The PCR products can then be transcribed into RNA, in which case the test sample nucleic acid as well as the probe consists of RNA. The PCR products can sometimes be added directly to an in vitro transcription reaction without purifying the template DNA. The RNA may be labelled after the transcription reaction, but preferably the RNA is labelled during transcription by the incorporation of radioactively labelled nucleotides. The reaction products can then be mixed and hybridized. As a result of this strategy, each of the two test sample strands would be labelled and hybridized to each of the two labelled probe strands. Specific cleavage of either hybrid would indicate the presence of a mismatch, i.e. a mutation. Specific cleavage refers to cleavage not seen in the control duplexes which do not contain mismatches.

In a modification of the above approach, the probe is derived from the transcription of endogenous sequences, co-amplified from genomic DNA isolated from a diploid cell. In a heterozygous mutant cell, this results in a co-amplification of both wild type and mutant sequences, which are then co-transcribed into RNA and self-hybridized. This generates both mismatch—containing RNA duplexes (the targets for RNase cleavage) and perfectly matched, RNase resistant duplexes. In a further modification, a small amount of wild type sequence may be added to the PCR during amplification of the genomic test sample, to provide sequences capable of generating mismatched duplexes with the products of a homozygous mutant cell.

Nucleic Acid Samples for Mismatch Analysis

Test sample nucleic acid may be derived from cloned or genomic DNA by any of the standard procedures known to those of skill in the art, and need not be purified to homogeneity. Typically the test sample DNA consists of a genomic or cDNA sequence amplified by PCR. As discussed above, by including phage promoter sequences on the primers used for amplification, the PCR products can be turned into templates for their own transcription into RNA. The RNA may be labeled by incorporation of radiolabeled or non-radiolabeled nucleotides during the in vitro transcription reaction. From the above descriptions, it can be seen that the distinction between probe nucleic acid and test sample nucleic acid is somewhat artificial, in that the probe may be derived from either endogenous or exogenous sources, and the test sample nucleic acid may be either DNA or RNA, and may be derived originally from either genomic DNA (by PCR) or from expressed mRNA (by RT-PCR). Those of skill in the art will appreciate that numerous permutations and modifications of the above methods may be used in the design of individual experiments, and these are understood to be within the scope and spirit of the present invention. For example, transcription of the two strands of a PCR product having opposable phage promoters may be performed separately or simultaneously. If performed simultaneously, the transcription reaction may contain two different phage RNA polymerases (for example T7 and SP6), or a single phage polymerase may be used if its corresponding promoter is added to both ends of the PCR product. Also, multiple templates may be co-amplified in a single PCR reaction (a process termed "multiplex PCR"), and if phage promoter sequences are included in or added to these products, they may then be co-transcribed in a multiple in vitro transcription reaction.

Hybridization

Standard annealing or hybridization procedures are described by Sambrook et al. (1989). Generally they entail two or more nucleic acids, for example probe and test sample nucleic acids, to be mixed together, denatured and then subjected to conditions in which complementary strands anneal, or base pair by hydrogen bonding to form double strands. The annealed strands are said to be hybridized. For example, the mixture may be heated to from about 90° C. to about 95° C. for about three minutes and then gradually cooled to a lower temperature, 42° C. for example, for a period of time sufficient to allow hydrogen bonding of the complementary strands. The time required for annealing of complementary strands depends on the concentration of each strand and will vary from a few minutes (for reactions where both probe an test nucleic acids are present at high concentrations), to several hours or overnight for reactions having at least one species present at low concentration. It is therefore advantageous to use high concentrations of probe and test sample nucleic acids, such as may be generated by PCR amplification and/or transcription of PCR amplified sequences.

Electrophoresis

Any standard agarose or polyacrylamide gel electrophoresis may be used to separate the cleavage products by size. The only requirement is that the products of the RNase treatment, where a mismatch was present, can be distinguished from the products of such treatment where no mismatches were present. The matrix size of the gels will be determined by the expected size of the nucleic acid products to be separated, as is well known to those of skill in the art. For example, the separation of large nucleic acid fragments requires a lower percentage of agarose or acrylamide in the gel, and the separation of small nucleic acid fragments requires a higher percentage gel.

Probe Detection

If the RNA probe is radioactively labelled, standard autoradiographic detection procedures may be used to detect the products after electrophoresis. Non-radioisotopically labelled probes should be detected by standard procedures appropriate for the particular type of label used, for example, using anti-digoxigenin antibodies for digoxigenin labeled probes, or streptavidin detection for biotinylated probes. Unlabelled probes may be visualized after staining the gel with ethidium bromide and exposing it to ultraviolet radiation. Since ethidium bromide staining is a relatively insensitive method of detection, this method is usually reserved for situations where high mass amounts of probe and test sample RNAs are used. Another option for direct visualization of protected fragments is silver staining the gel.

Development Of A Quantitative Assay For RNase Activity

A reliable RNase activity assay that could be used under a variety of experimental conditions was a necessary antecedent to the present invention. In particular, a constant enzymatic activity was needed over a range of conditions such as different salt concentrations. This would allow the generation of results that could be standardized and would allow the direct comparison of the efficiencies of different ribonucleases.

A substantial amount of effort was required to arrive at the standard assay disclosed herein and used in the development of the present invention. Spectrophotometric assays were considered, but these are relatively insensitive and require large amounts of enzyme and substrate. Sensitivity can be increased by coupling the RNase cleavage reaction products to colorimetric enzyme amplification steps, but these would have been incompatible with the wide variations in reaction conditions that needed to be tested. Precipitation based assays are more sensitive, but have limitations related to their non-linearity at extremes of enzyme:substrate ratio.

Given the limitations of the other methods, a midpoint assay was used to assess RNase activity within the linear dose-response range. The standard assay measures degradation of a $^{32}$P-labeled single-stranded RNA tracer in reactions with total yeast RNA as substrate. Within the present invention, one unit of activity is defined as the amount of RNase needed to degrade 50% of the $^{32}$P-labeled tracer in a 20 µl reaction containing 2 µg of yeast RNA, after 30 minutes incubation at 37° C. Isopropanol was used to precipitate duplicate samples because isopropanol precipitates fewer free cpm than ethanol and permits greater recovery of the tracer in the no-RNase control reactions than does TCA precipitation. One unit of activity under optimum conditions for each enzyme was found to require about 0.5 ng of RNase A and 1.2 ng of RNase I. In some later studies, a qualitative rapid activity assay was used in which RNase-treated yeast RNA samples were analyzed directly on agarose gels in the presence of ethidium bromide.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

Effect of NaCl on RNase Activity

Since the inventors contemplated that the salt concentration would be a major variable in mismatch detection assays, the effect of NaCl on RNase activity was investigated. FIG. 1 shows the results of varying NaCl up to 300 mM in the standard assay described above using RNase A and RNase I. In the figure, the solid line represents RNase A activity and the dotted line represents RNase I activity. The data indicates that as the concentration of NaCl increases from 0 to 300 mM, the activity of RNase A decreases over the entire range of salt concentrations. RNase I activity increases in the range of 50 mM to about 150 mM NaCl and then decreases slightly at the higher salt concentrations.

In these reactions, duplicate 20 µl reactions contained 2 µg of total yeast RNA, $10^5$ cpm of gel-purified 300 base synthetic transcript ($^{32}$P-labeled to $10^8$ cpm/µg), and one–two units of RNase A or RNase I. Reaction buffers contained 20 mM Tris, pH 7.5, and increasing concentrations of NaCl as indicated in FIG. 1. After 30 minutes incubation at 37° C., reactions were stopped by addition of two volumes of solution containing guanidinium thiocyanate and isopropanol and 5 µg of carrier DNA. Reactions were chilled 15 min at −20° C., centrifuged 15 min at 15,000× g, and supernatant fluids were removed by gentle aspiration, mixed with aqueous fluor, and counted in a scintillation counter. Pellets were dissolved in 50 µl of water with vigorous vortexing and heating and counted in the same way. The number of counts in the supernatant was divided by total counts (pellet plus supernatant) for each sample, and this ratio was plotted against NaCl concentration in the reaction. The no-RNase controls showed about 5% release of label into the supernatant.

For RNase A, it was found that optimal activity is maintained below 75 mM NaCl. Increasing the NaCl concentration results in a sharp decline in activity to about 15% of optimum at 300 mM. The effect of NaCl on RNase I is less dramatic. RNase I activity is optimal at about 100 mM, falling off to 60% at 10 mM NaCl and declining to about 80% at 300 mM. Other variables tested (for example, pH, formamide, MgCl$_2$) caused less than a two-fold difference in RNase activity over the ranges tested.

EXAMPLE II

Effect of NaCl on Ability of Duplex RNA to Resist RNase Digestion

The success of RNase protection in detecting mismatches depends on the ability of the enzyme to specifically cleave a single unpaired base in a duplex RNA molecule. Since NaCl concentration is known to have a major effect on the structure and stability of double-stranded RNA, the inventors felt it was necessary to determine empirically the threshold NaCl concentration above which hybridized RNA probes would form a stable duplex.

Stability is defined operationally as resistance to ribonuclease digestion. The substrates for these stability studies, and for the mismatch assays to be described, were hybridized in vitro transcripts containing 266 bp of p53 exon 5 or 192 bp of exon 7 sequence, flanked by about 10 bases of G-C rich duplex derived from the PCR overlap extension reaction, and about 25 nucleotides of phage promoter-complementary single-stranded tails. The exon 5 and exon 7 sequences contained 61% and 57% G-C, respectively. Stability was assessed by autoradiography of the cleavage products after RNase digestion and electrophoresis on denaturing acrylamide gels. To accurately quantify results, the release of free $^{32}$P into the supernatant after RNase digestion was determined in some studies. However, the major assessment of duplex stability was made by directly examining the autoradiograms. This type of assessment was considered to be the most relevant for providing information for optimizing cleavage at mismatches.

Figure 2A:
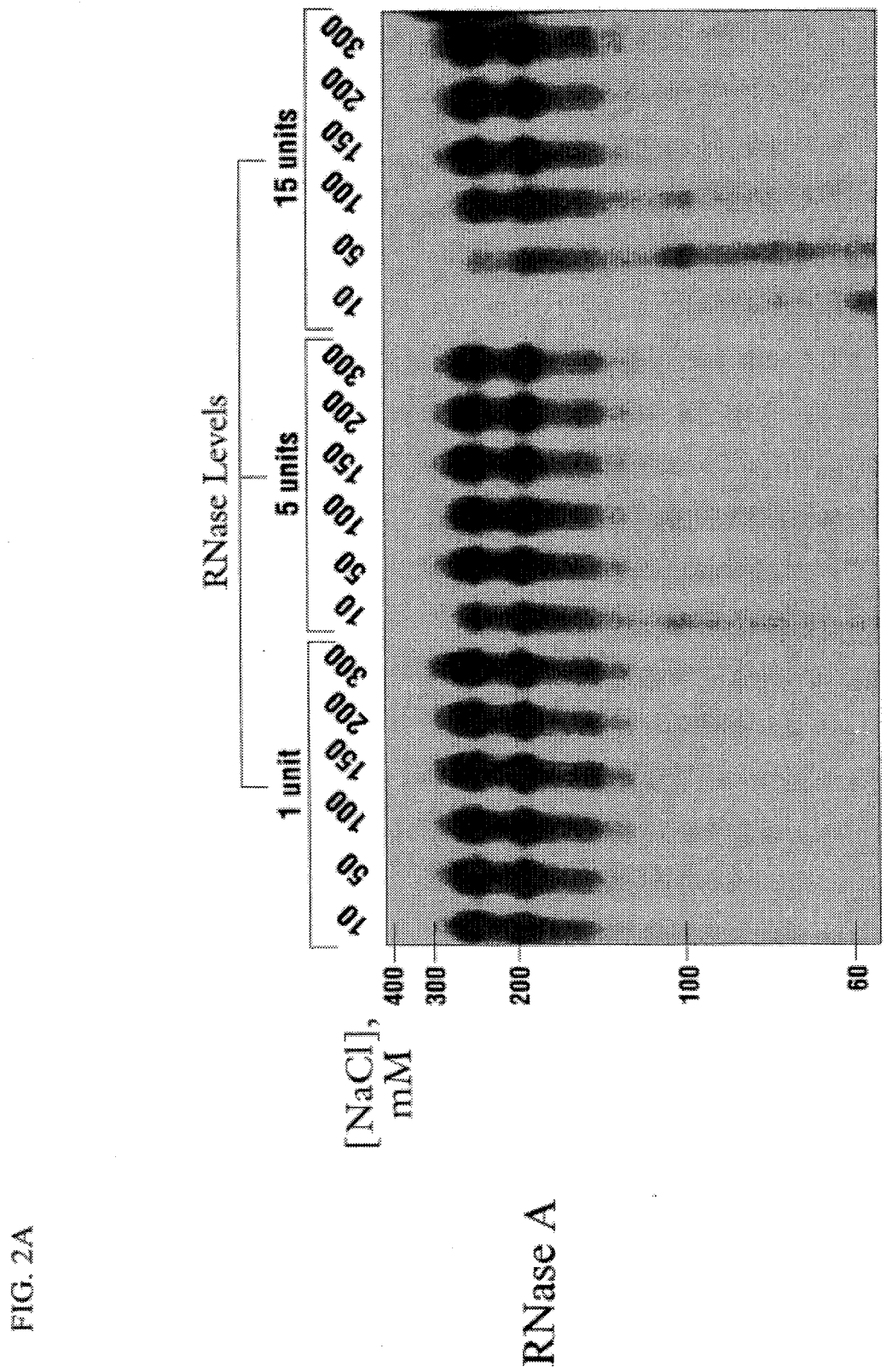
FIG. 2A shows the stability to RNase A digestion at levels of 1 unit, 5 units and 15 units RNase per reaction at various NaCl concentrations.
Figure 2B:
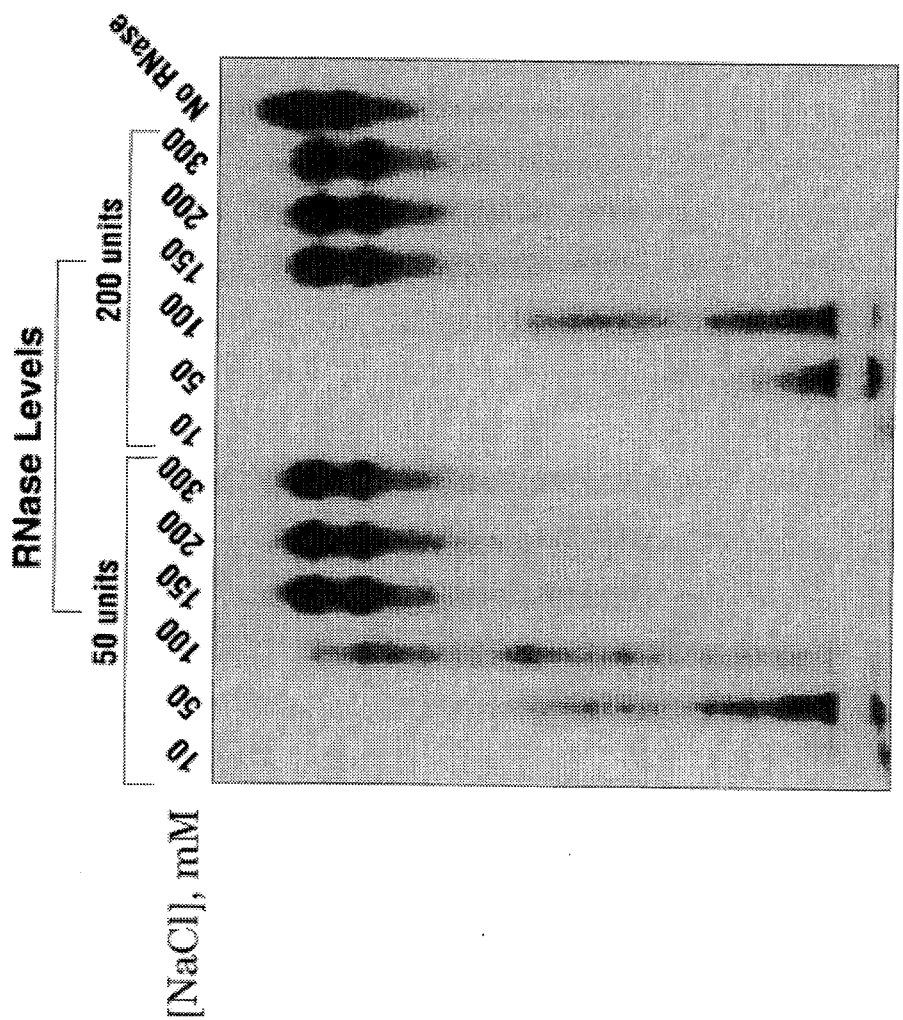
FIG. 2B shows the stability to RNase A digestion at levels of 50 and 200 units RNase per reaction at various NaCl concentrations.

The results of a typical duplex stability assay with perfectly matched duplex RNA is shown in FIG. 2. In gels A and B, each panel of six lanes shows duplexes treated with a given amount of RNase A (indicated at the top of each panel) at six different NaCl concentrations (indicated above each lane, in mM). In gel C, each panel of four lanes shows duplexes treated with a given amount of RNase I (indicated at the top of each panel) at four different NaCl concentrations (indicated above each lane, in mM).

RNA duplexes were made by mixing complementary sense and antisense strands of $^{32}$P-labeled ($10^8$ cpm/μg) gel purified p53 exon 5 or exon 7 transcripts in hybridization buffer (80% formamide, 300 mM Na-acetate pH 6.4, 100 mM Na-citrate pH 6.4, 1 mM EDTA), heating at 95° C. for 3 minutes, and incubating overnight at 42° C. Aliquots (~5×10$^4$ cpm) of the hybridized exon 5 and exon 7 duplexes were diluted 20-fold into digestion buffers containing RNase, 20 mM Tris, pH 7.5, and increasing amounts of NaCl as indicated. At each NaCl concentration tested, duplexes were challenged with five different levels of RNase A or RNase I (1 unit, 5 units, 15 units, 50 units, or 200 units). The actual amounts of RNase added to each reaction were adjusted to compensate for effects of NaCl on the enzyme (for example, one unit of RNase A at 300 mM NaCl required a 6.7-fold greater mass amount of the enzyme than at 50 mM NaCl). Reactions were incubated for one hour at 37° C., then terminated and precipitated as above, except that pellets were resuspended in 8 μl of gel loading buffer (80% formamide/2 mM EDTA/0.1% each xylene cyanol and bromophenol blue), heated 3 minutes at 95° C., and electrophoresed on 5% polyacrylamide/8M urea gels at 250–300 volts for about 45 minutes. Gels were transferred to chromatography paper and exposed directly to X-ray film without fixing or drying.

It is clear that duplex stability is a function not only of NaCl concentration, but also of the amount of RNase used to challenge the duplex. Thus, for example, RNA duplexes that are largely resistant to degradation by 5 units of RNase A in 50 mM NaCl are almost completely degraded by 15 units RNase A at the same NaCl concentration (FIG. 2a). Since the activity of the RNase A was itself influenced by NaCl, the amount of RNase was adjusted so that there would be constant RNase activity at each NaCl concentration. Thus, for comparing duplex stability at a given RNase level in 50 mM vs 300 mM NaCl, a 6.7-fold greater mass of RNase A was added to the reactions containing 300 mM NaCl since RNase A is only 15% as active at 300 mM NaCl as at 50 mM NaCl. It can be seen that above 150 mM NaCl, the RNA duplexes were mostly stable up to the highest amount of RNase A tested (200 units=33.5 mg/ml). At lower NaCl concentrations, duplex stability was extremely sensitive to the amount of RNase A used. At the lowest NaCl levels tested, the duplex was not stable to RNase A amounts above 1 unit (approx. 20 ng/ml). No differences in threshold NaCl concentration for stability were seen between the exon 5 and exon 7 duplexes. Preliminary results with an A:U rich (64%) duplex from the APC gene suggest that duplex stability curves similar to those in FIG. 2 can be achieved by reducing RNase concentration 5–10 fold, or increasing NaCl concentration 3–5 fold. It should be noted that all RNase digestion reactions also contained carry over components of the hybridization reactions, which were diluted 20-fold into the RNase digestion buffer. All reactions therefore also contained 4% formamide, 15 mM acetate, and 5 mM citrate as sodium salts.

Figure 2C:
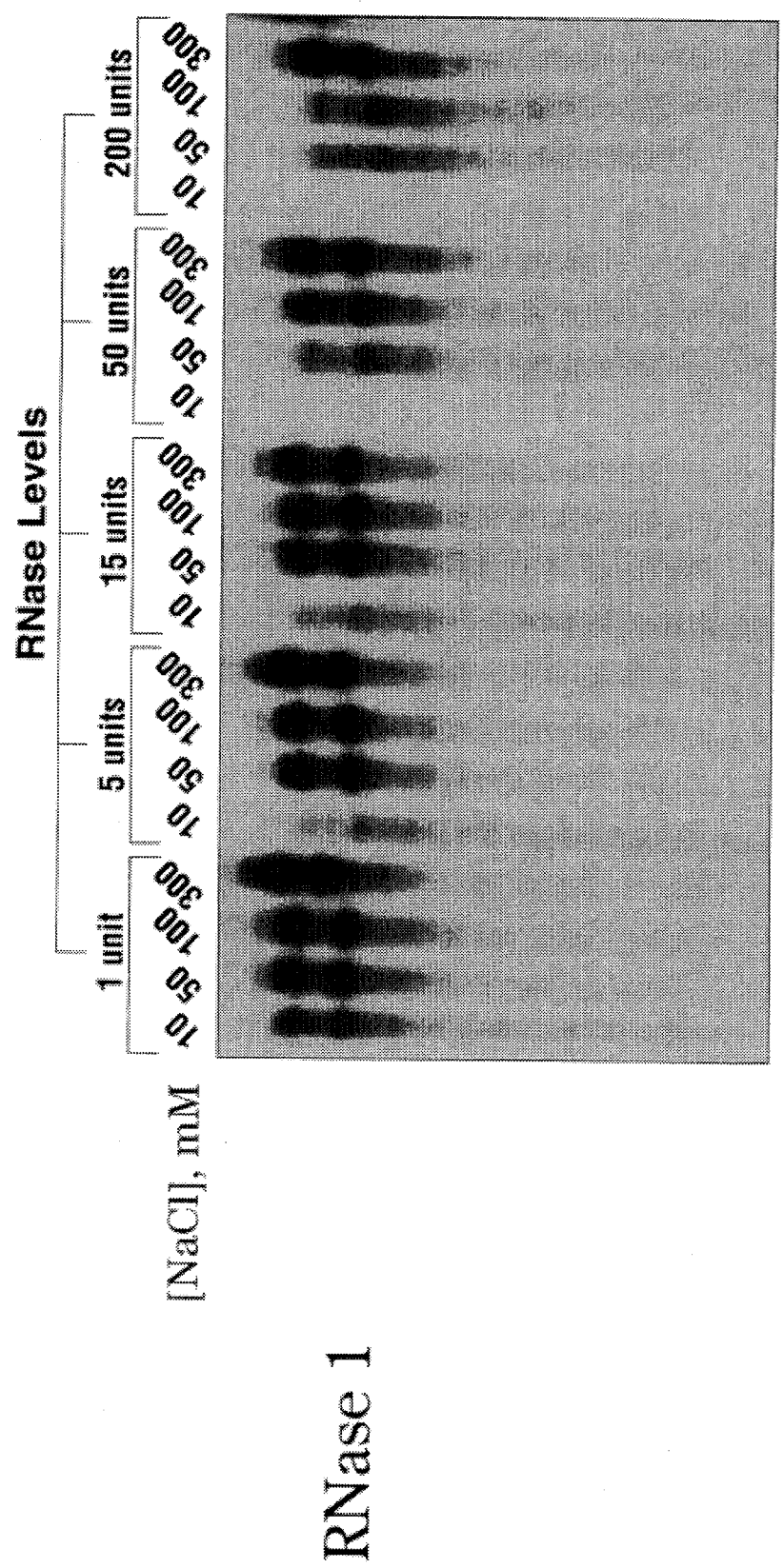
FIG. 2C shows the stability to RNase I digestion over the range of 1 to 200 units RNase per reaction at various NaCl concentrations.

When the same duplex stability experiment was repeated using RNase I instead of RNase A, a slightly different result was seen. FIG. 2C shows that the perfectly matched duplexes remained stable over the whole range of NaCl concentrations tested in the presence of RNase I activity (which was again normalized for each salt concentration) ranging from 1 to 15 units. The RNA duplexes tested were thus stable to RNase degradation over a somewhat broader range of NaCl concentrations for RNase I than for RNase A. This observation may point to a fundamental difference in the mechanism by which these enzymes initiate cleavage at susceptible regions of the duplex (probably A-U rich regions, the ends of molecules, and possibly nicks). A key finding from these experiments is that RNA duplexes can remain resistant to RNase degradation at very low NaCl concentrations, provided the RNase level is reduced accordingly. The low RNase levels are still quite adequate to completely digest the single-stranded "tails" of 25 nucleotides that flank the base-paired regions of the hybridized transcripts as seen by the slightly reduced mobility of the no-RNase control duplexes compared to the RNase-digested stable duplexes. (The tails are due to the fact that transcription from each promoter initiates at about the 25th base from that end, and terminates after transcribing the complement of the opposite-end promoter.)

EXAMPLE III

Optimizing NaCl and RNase Concentrations for Cleavage at Mismatches

Mismatch cleavage in RNA/RNA duplexes was tested by cross-hybridizing complementary $^{32}$P-labeled sense and antisense transcripts made from normal and p53 point-mutation-containing DNA templates. These templates were amplified by the polymerase chain reaction (PCR) from a collection of mutants obtained from Dr. Ken Kinzler (The Johns Hopkins Oncology Center, Baltimore, Md.). However, as mentioned earlier, the templates for the probes and test sample nucleic acids may be obtained form any source desired. Phage promoters (T7 and SP6) were added to opposite ends of the PCR product to permit both strands of the probe and test sample sequences to be converted into RNA. Megascript™ and Maxiscript™ in vitro transcription kits (Ambion, Austin, Tex.) were used to transcribe the PCR products, and the reactions were treated with DNase to remove the template DNA after RNA synthesis was complete. The PCR product was then added directly to the in vitro transcription reactions without purification of the DNA. The products of the transcription reactions were then mixed and hybridized, generally without purification of the RNA. Hybridization occurred rapidly because of the high concentration of the probe and test sample RNA molecules. Thus, each of the two mutant strands was converted into labeled RNA and hybridized with a labeled wildtype complement RNA. Cleavage of either strand of either hybrid would result in detection of the mutation. This strategy allowed the efficient detection of all mismatches tested and it provided confirming data from both strands of the test sample gene.

To avoid the expense of adding the ~25 base T7 and SP6 promoter sequences directly to each primer pair used in the PCR reaction, the overlap extension method was used to append generic promoter cassettes to the different templates (Horton et al., 1989). The promoter sequences and amplified exons were joined during PCR by overlap at common 10 bp G-C rich sequences that also contained the transcription initiation sites. As will be understood by those of skill in the art, amplification primers can also comprise the promoter sequences so that the promoters can be added to the amplified products in a single conventional PCR step, and that such primers which include the promoter sequences are also encompassed by the present invention.

EXAMPLE IV

Dynamic Range of RNase A vs RNase I

During the course of the present studies, the inventors began using much lower specific activity probes, which allowed the use of a single probe preparation for over a month. However, this meant that the RNase digestion reactions contained about a 50-fold greater mass amount of substrate RNA than when the activity of the RNases was assessed in the duplex stability experiments. The decrease in enzyme to substrate ratio (although not in absolute enzyme concentration) did not change the previously determined optimum concentrations for mismatch detection using RNase A, but for RNase I this change caused the enzyme level to be suboptimal. This was discovered because of the altered mobility of the duplexes due to failure of the relatively lower RNase I level to degrade the 25 base single-stranded tails at the ends of the duplexes. For equivalent mismatch cleavage, RNase I concentration had to be increased about 5-fold to compensate for the increase in substrate concentration. This result confirms other studies that show that RNase A has a much wider dynamic range than RNase I in terms of its effective concentration in conventional RNase protection assays, and it reinforces the idea of a fundamental difference in mismatch recognition and/or cleavage mechanisms between the two enzymes.

EXAMPLE V

Comparison of Cleavage Specificities of RNase A and RNase I

Since RNase I cleaves after all four bases while RNase A is thought to cleave only at pyrimidines, it is expected that RNase I would be able to cleave both strands of an RNA duplex containing an A:C mismatch, while RNase A should only cleave the strand containing the C residue. This hypothesis was tested by hybridizing complementary transcripts which were radiolabeled to specific activities differing by 100-fold; this allowed the accurate quantification of both transcripts, while visualizing only the mismatch cleavage products from the higher-specific activity transcript on the autoradiogram. In this way, it was possible to distinguish which strand was being cleaved.

Duplexes containing an A:C mismatch and having either the sense or antisense strand labeled to the higher specific activity were treated with various amounts of RNase A or RNase I under several salt conditions. Surprisingly, both RNase I and RNase A are able to cleave both strands essentially to completion, to generate the expected subfragments. Complementary p53 exon 5 transcripts, $^{32}$P-labeled to high (~$10^8$ cpm/µg) and low (~$10^6$ cpm/µg) specific activities, were hybridized to generate duplexes containing an A:C mismatch. The duplexes differed in whether the high specific activity strand contained the A or the C residue of the mismatch. Aliquots of the duplex RNAs were treated with various concentrations of RNase A or RNase I at various NaCl levels.

These tests demonstrated that there was no preference for RNase A to cleave the strand having the mismatched pyrimidine over the mismatched purine-containing strand. With RNase A, the smaller subfragment migrates slightly slower when it is generated by cleavage of the A-mismatched strand than when produced by cleavage of the C residue. This could be due to slight intrinsic mobility differences between the complementary strands, or to a real difference in size due to asymmetric cleavage. In the latter case, the asymmetry would presumably be due to cleavage at a nearby pyrimidine instead of at the mismatched A residue. These results are consistent with the findings that RNase A appears to cleave both strands of a mismatch whenever the sample is double-stranded RNA. It should be noted that compared to the RNase A lanes, the RNase I digested samples show more nonspecific cleavage of the no-mismatch control duplexes and more degradation of the expected subfragments, especially the smaller one. The important implication of these findings is that, using the RNA/RNA reciprocal probe/sample strategy of the present invention, the detection efficiency is doubled over what would be obtained if only one strand was cleaved. This of course also applies to the situation where a single labeled RNA probe is hybridized to unlabeled total RNA isolated directly from cells.

EXAMPLE VI

Detection of Mismatches Generated by Transition Mutations

Since transition mutations are more common in nature than transversions (Lewin, 1983), the G:U—A:C mismatch complement is by far the most common of the four possible sets of reciprocal single-base mismatches (the other three sets being A:G—C:U, A:A—T:T, and C:C—G:G). Earlier work had suggested that A:C mismatches were among the easiest to detect and G:T and G:U the most difficult (Myers and Maniatis, 1986).

Figure 3A:
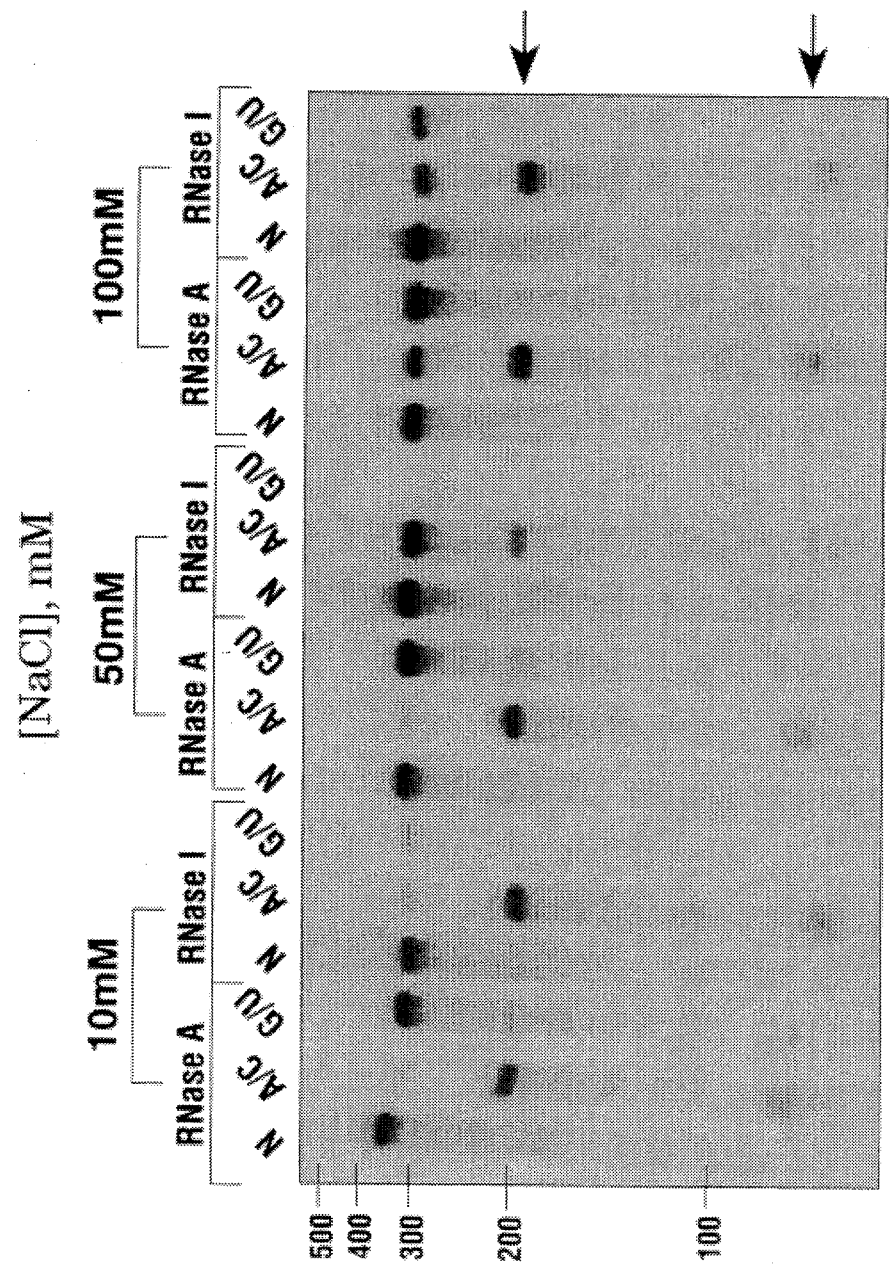
FIG. 3A is a representative gel from a 16 gel matrix in which the ability of the present method to detect transition mutations was tested. This gel is the result of digestion with 1 ng RNase per reaction at various NaCl concentrations.
Figure 3B:
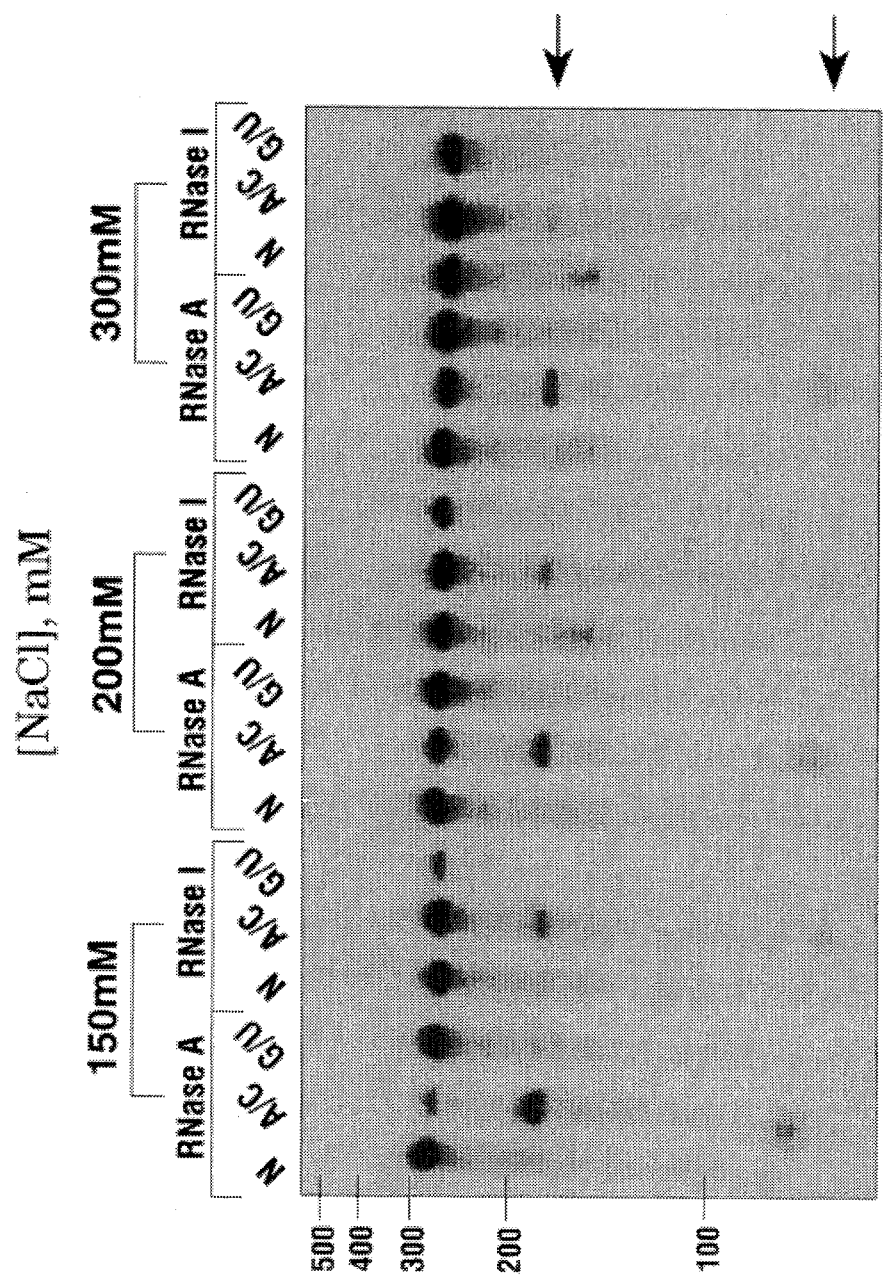
FIG. 3B is another representative gel from the 16 gel matrix as is FIG. 3A. This gel contains the results of digestion with 5 ng of RNase at various concentrations of NaCl.

The set of four duplexes initially tested consisted of two perfectly matched control duplexes and two duplexes having either a G:U or an A:C mismatch at codon position 173, due to a G to A transition in the mutant template. Each of the four duplexes, having either G:U, A:C, A:U, or C:G at the codon 173 position, was challenged with 5 different concentrations of either RNase A or RNase I, ranging from one to 200 units, under 6 different conditions of NaCl concentration varying from 10 mM to 300 mM. As before, the mass amounts of RNase added were adjusted to compensate for differences in activity at each NaCl concentration. FIG. 3 shows representative gels that illustrate the reciprocal effects of raising RNase concentration and reducing NaCl concentration. In the gels in FIG. 3, p53 exon 5 duplexes containing no mismatch (lanes labeled N), an A:C mismatch, or a G:U mismatch were treated with the indicated amounts of RNase A (left 3 lanes of each panel) or RNase I (right three lanes) as described in the preferred embodiment section (supra), in reactions containing various concentrations of NaCl as indicated above each panel. Positions of subfragments generated from mismatch cleavage are indicated by arrows. RNase A can cleave the A:C mismatch over a wider range of NaCl concentrations compared to RNAse I, at a constant RNase level. The proportion of full-length, uncleaved duplex in the A:C lanes increases at a given RNase level as salt is increased. Molecular size standards are $^{32}$P-labeled RNA transcripts of Ambion's (Austin, Tex.) RNA 100 base ladder template set.

Based on the data represented in FIG. 3, it is concluded that both RNase I and RNase A are able to cleave the A:C mismatch to give the expected subfragments, although with both enzymes the smaller fragment runs with an apparent mobility about 20% greater than expected. As NaCl concentration is increased, more of each enzyme is required for mismatch cleavage. RNase A is able to detect the A:C mismatch at NaCl concentrations ranging from 10–300 mM, but a 1300-fold greater mass amount (corresponding to a 200-fold greater activity) is needed at 300 mM compared to 10 mM NaCl. With RNase I, there is very little A:C cleavage at NaCl concentrations above 150 mM, regardless of how much the enzyme level is increased.

Cleavage of the A:C mismatch is more complete and more specific with RNase A than with RNase I. As NaCl varies between 10 mM and 300 mM, increasing RNase A levels can be chosen that convert almost all of the 266 bp duplex to the expected subfragments.

In a further experiment, the RNase I conditions were optimized. Complementary $^{32}$P-labeled 485 transcripts comprising the p53 exon 54 to intron 5 to exon 6 genomic region were hybridized and treated with the indicated amounts of RNase I in buffers containing various concentrations of NaCl as indicated. After incubation for 30 minutes at 37° C., the RNase was inactivated and the digestion products recovered by alcohol precipitation and analyzed on a 5% denaturing polyacrylamide gel. There was complete degradation of the duplexes at high RNase/low NaCl conditions, and failure to cleave the A-C mismatch at high RNase/high NaCl conditions.

Figure 4A:
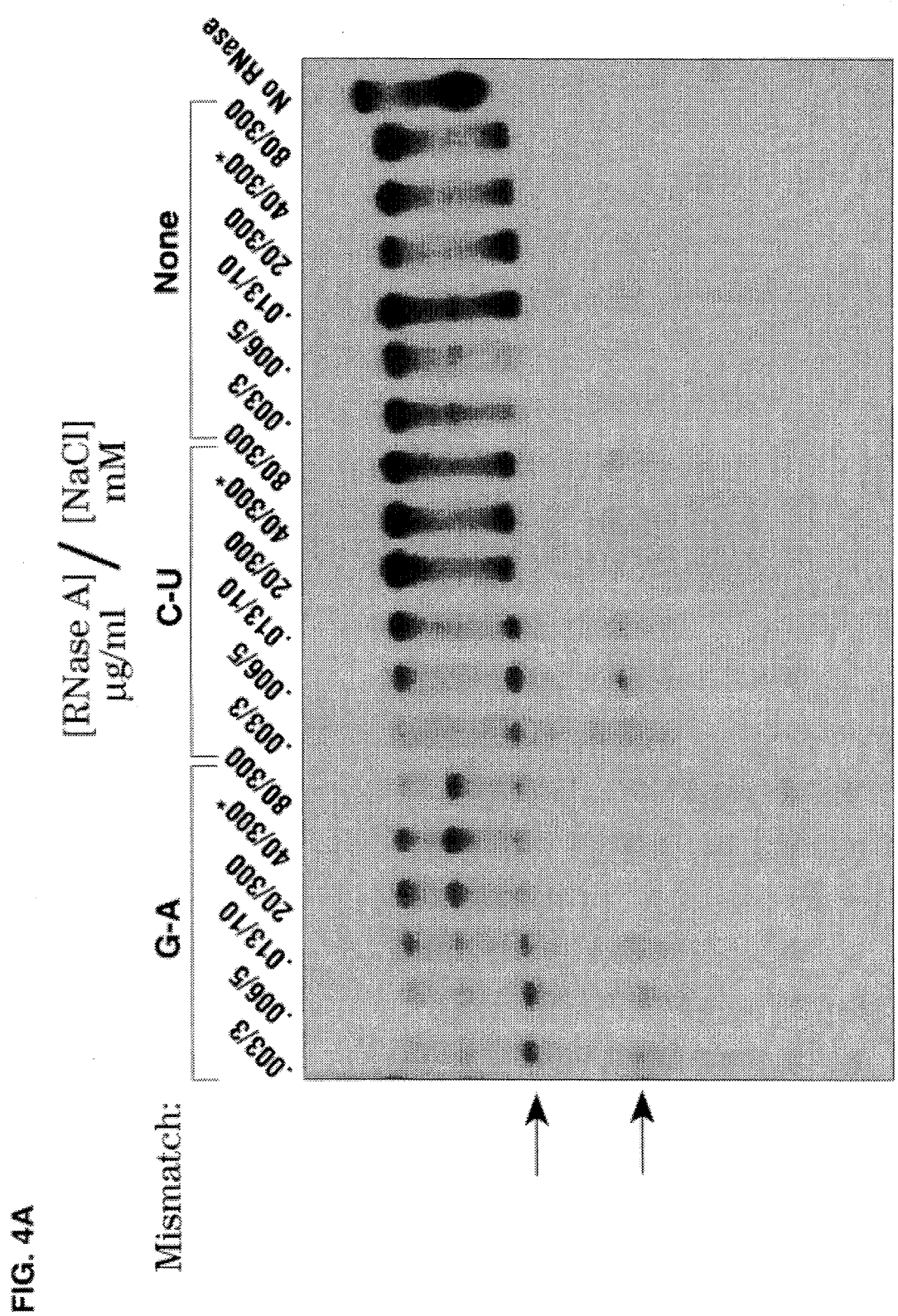
FIG. 4A is the results of digestions of G-A and C-U mismatches by RNase A in various enzyme/salt concentrations.
Figure 4B:
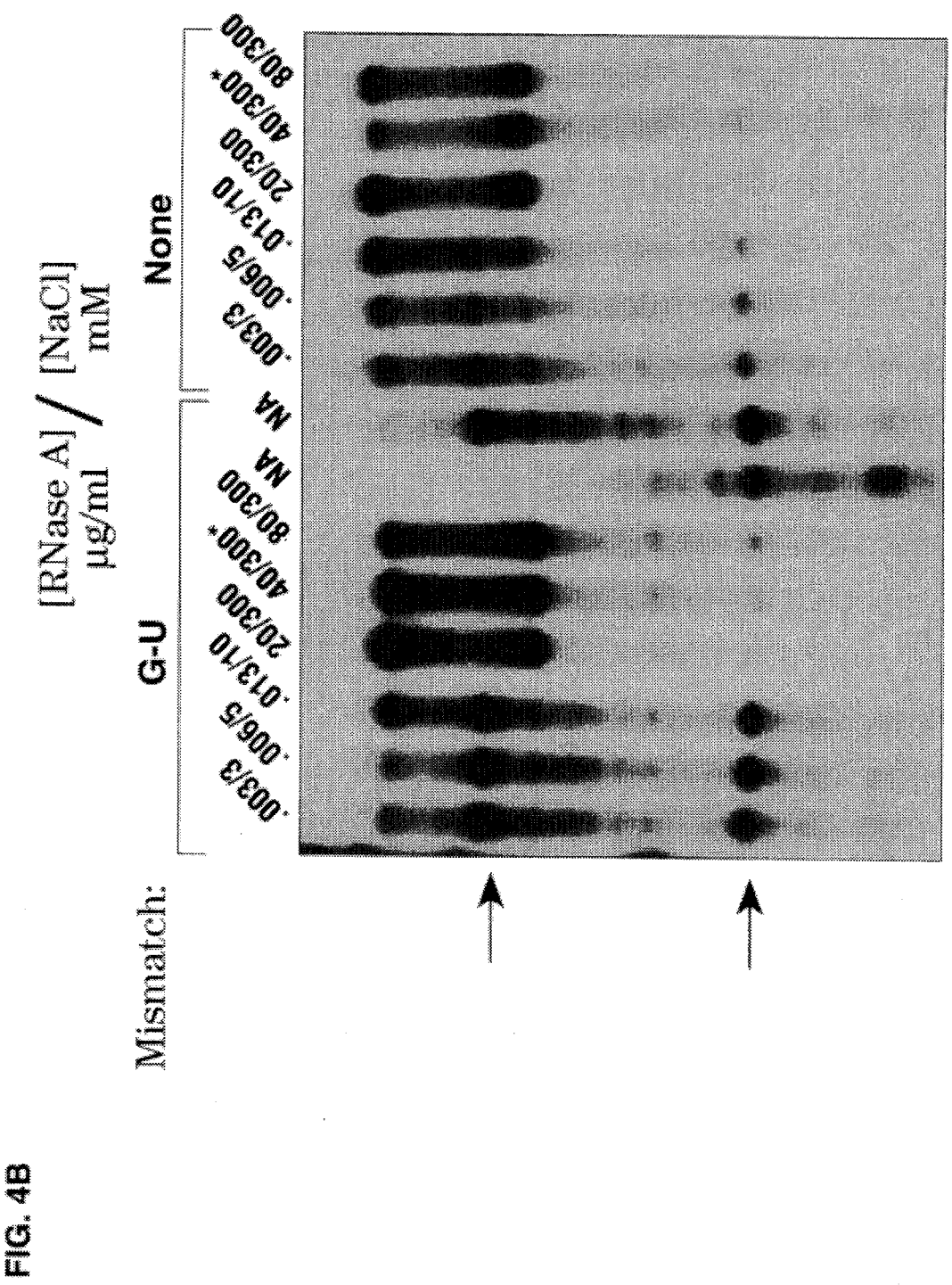
FIG. 4B is the results of digestions of G-U mismatches by RNase A in various enzyme/salt concentrations.
Figure 4C:
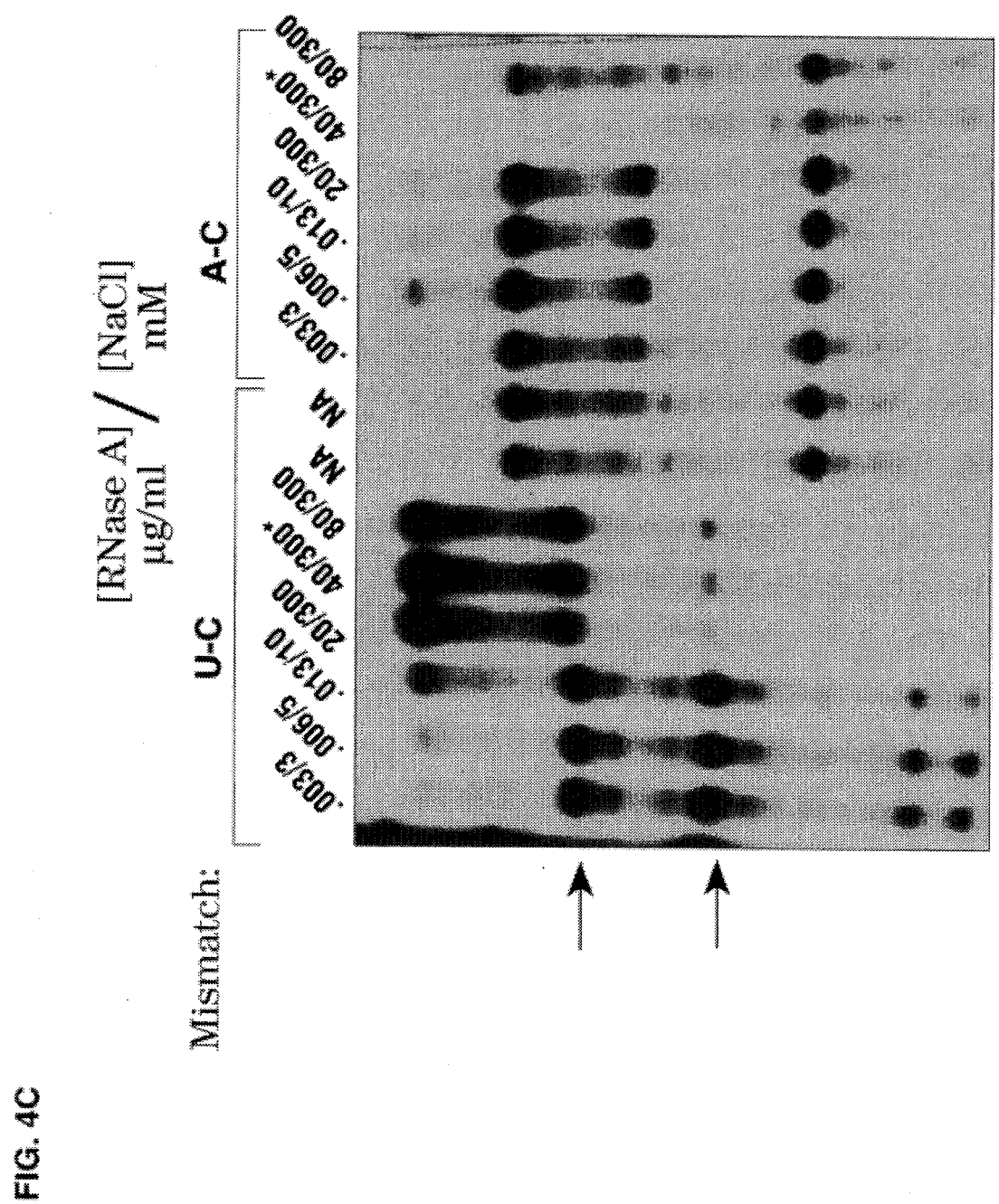
FIG. 4C is the results of digestions of U-C and A-C mismatches with RNase A in various enzyme/salt concentrations.
Figure 4D:
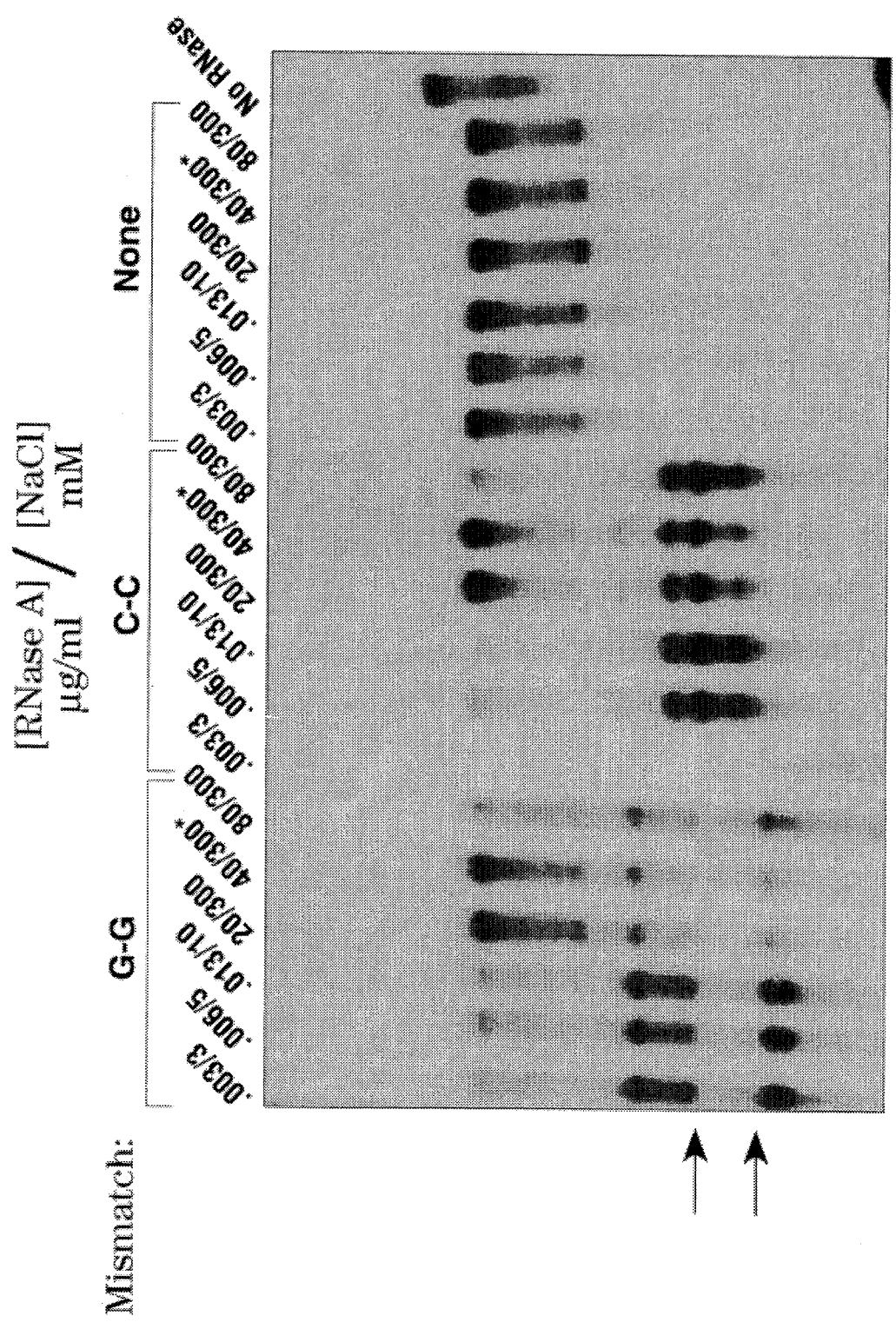
FIG. 4D is the results of digestions of G-G and C-C mismatches with RNase A in various enzyme/salt concentrations.

There is no cleavage by RNase I at the G:U position under any condition tested, and only a modest amount (10–20%) of G:U cleavage over background for RNase A, under the lowest NaCl/RNase A digestion conditions tested. However, in subsequent experiments, cleavage of the G:U mismatch by RNase A was improved by reducing enzyme and NaCl levels even further (see FIG. 4b).

Increasing NaCl concentration above 150 mM results in very little change in the cleavage products as either RNase A or RNase I is increased from lowest to highest amounts. Most of the effects, in terms of large variations in cleavage pattern with small variations in RNase concentration, were in the 10–50 mM NaCl range.

EXAMPLE VII

Detection of Mismatches Generated by Transversion Mutations

Four of the six possible mismatches which result from a transversion mutation were tested under a range of NaCl/RNase conditions (the rare A:A—U:U mismatch complement was not present in the collection of p53 mutants, and thus was not tested). As with the transition mutations tested above, combinatorial hybridization between the 2 strands of each wildtype and mutant probe allowed pairwise assessment of the reciprocal mismatches (G-G and C-C or A-G and C-U) that resulted from each transversion mutation.

With RNase A, the best conditions for cleavage of the A:G, C:T, C:C, and G:G mismatches were with RNase A levels between 3–25 ng/ml in 3–10 mM NaCl. Within that range, the different mismatches seem to have only slightly different optima for detection. Under standard conditions practiced prior to the present invention, for example 40 µg/ml RNase A in 300 mM NaCl, cleavage is absent at the G:U, C:U, G:G, and A:G mismatches and inefficiently detected at the C:C mismatch. Increasing RNase A to 80 µg/ml, at which point the perfectly matched duplex begins to show degradation, failed to improve mismatch cleavage except for the C:C mismatch.

The data in FIG. 4 summarize these results. Microgram amounts of $^{32}$P-labeled (~$10^5$ cpm/µg) complementary p53 exon 5 and exon 7 transcripts from normal and mutant templates were hybridized and treated with the indicated amounts of RNase A or RNase I in buffers containing various concentrations of NaCl as indicated. Gels were exposed to X-ray film for several hours with screens, or overnight without screens. For all gels, RNase and NaCl conditions used in each digest are indicated above the lanes, in µg/ml for RNase and millimolar concentration for NaCl. In each panel, RNase and NaCl levels increase from left to right (except Gel E where right hand lanes contain high RNase I in low NaCl). Arrows show positions of subfragments produced by mismatch cleavage. Asterisks indicate standard reaction conditions (40 µg/ml RNase A in 300 mM NaCl). Gels A–D are RNase A treated samples and Gel E is RNase I treated samples.

Note that the p53 exon 5 RNA duplexes often (but not always) migrate as two species, whether or not they are treated with RNase. The two main bands represent the extremes of mobility (at about 300 and 150 bases), with a heterogeneous smear of species with intermediate mobilities running between them. This phenomenon has occurred in the published data of other investigators using other probes (for example Nishisho et al., 1991). Even when gel-purified single-stranded complementary transcripts migrating at the expected position of ~300 nucleotides were hybridized, the resulting duplexes migrate as two bands on denaturing gels, which suggests that the different species exist in equilibrium between two different secondary structures. Both species are substrates for mismatch detection, as they both disappear and give rise to the expected subfragments when cleaved at the mismatch position. Some of the agents we have tested in our mismatch cleavage assays (spermidine, $ZnSO_4$, $MgCl_2$)

seem to push the equilibrium toward one form or another. It is contemplated that, with only routine experimentation, conditions can be identified under which there will be only one ossiform.

Figure 4E:
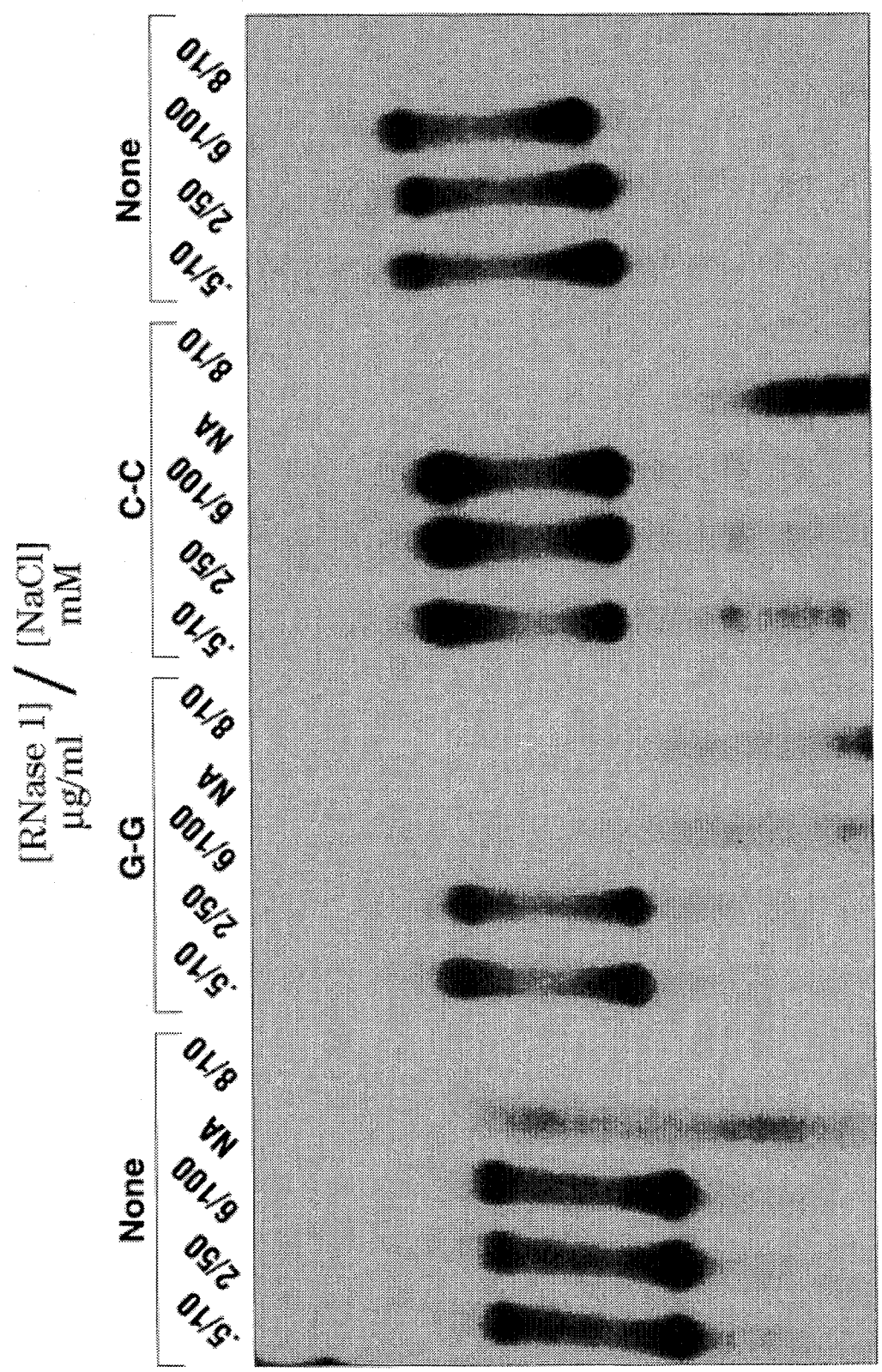
FIG. 4E is the results of digestions of G-A and U-C mismatches with RNase I in various enzyme/salt concentrations.

RNase I was also tested for cleavage of A:G, C:U, C:C, and G:G mismatches (representative data shown in FIG. 4E). Cleavage was detected only at the G:G mismatch and only under low salt/low RNase conditions, but the cleavage did not generate discrete subfragments. Increasing RNase I levels caused non-specific degradation to increase without a detectable increase in mismatch cleavage.

In four different cases where an expected mutation was not detected by this method, subsequent DNA sequencing showed that the presumed mutation was absent from the clone used to generate that template. This is explained by the fact that the normal allele was present in the tumor tissue from which the p53 clones were derived. The mismatch detection assay was thus shown to be reliable for screening both positive and negative samples. The inventors have not seen any evidence of "false positives" or other undesirable effects attributable to PCR errors. It is envisioned that, in general PCR errors would probably not result in cleavage products that would be detectable above background.

EXAMPLE VIII

RNase Protection in Conjunction with PCR

It is contemplated that the improved ribonuclease protection assays described herein would be especially powerful when coupled with PCR to generate sample DNA for analysis. This would circumvent the problem of isolating intact RNA for analysis, which is frequently difficult with clinical samples. In this method, both the sense and antisense DNA strands of the sample sequence and the sense and antisense strands of the probe are amplified by PCR using, preferably PCR primers that also incorporate the phage promoters to be used in the transcription reactions. Alternatively, the phage promoters may be added to the PCR products by the overlap extension method, or by ligation of synthetic annealed oligonucleotides. The products of both PCR reactions can then be added to the transcription reactions without being further purified. After transcription and hybridization of the transcription products, any cleavage by RNase under the conditions of the present disclosure will indicate the presence of a mutation.

EXAMPLE IX

A Kit for Use in Detecting Single Base Changes in a Nucleic Acid Sequence

Further aspects of the invention concern kits for use in detecting single base changes in nucleic acid sequences. Such kits may have as one component an enzyme or enzymes capable of specific cleavages of single stranded RNA and capable of detecting single base mismatches in an RNA/RNA or RNA/DNA duplex. The enzyme may be RNase A, RNase I, a modified version of one of the mentioned RNase enzymes, or a combination of these enzymes, or even a distinct RNase. Most preferably, the enzyme will be RNase A or a mixture of RNase A and RNase B. Other components of the kit may include, but are not limited to a solution of enzyme buffer and/or a solution of NaCl. Sterile, nuclease free, purified water may also be included in the kit. The enzyme or enzymes may be provided in lyophilized, powdered form to be stored in a freezer at about −20° C. to about −80° C. and to be mixed with solvents in the indicated concentrations just prior to use, or alternatively, the enzyme or enzymes may be provided in solution in an appropriate buffer and possibly glycerol solution. All of the said solvents and buffers may or may not be provided with the kit.

The kit may also contain a control DNA template(s) with and/or without a mismatch with a complementary RNA probe which may also be included in the kit. The RNA and DNA molecules will be provided in solution or in lyophilized form and would be stored at 4° C. or alternatively could be stored at −20° C. to −80° C.

The kit may also contain PCR primers to be used to amplify the test sample DNA and possibly to be used to amplify the control DNA. The primers will preferably be comprised of phage promoter sequences to be used in the transcription of the PCR products. The primers may also comprise sequences complementary to the regions of test sample DNA being amplified.

EXAMPLE X

Point Mutation Analysis of Genes

The compositions, techniques and kits of the present invention may be used to detect mutations in virtually any DNA or RNA segment of between 50 bases and about 2 kilobases. Thus, this improved technique will be useful in screening genes for mutations associated with many human cancers, such as, for example, mutations in p53, ras, neu, myc, abl, and other disease-associated mutations in these or any other genes, including HIV reverse transcriptase and β globin. Other genes that may be screened for mutations include, but are not limited to APC, which is thought to be associated with early events in the colon cancer pathway (Joslyn et al., 1991), and NF1, the gene implicated in neurofibromatosis (NF). The ability to accurately detect mutations, including single base mutations in these and other regulatory and structural genes will be useful in detection, therapy and counseling associated with a wide variety of genetic disorders.

In addition to the clinical and genetic counseling applications, the present invention will be useful as a rapid, accurate and economical screening method to detect mutations in studies of protein structure and folding, enzymatic mechanisms, RNA structure, antibody-antigen recognition and binding studies involving proteins, DNA and RNA. This would include, but is not limited to mutations created by site-directed mutagenesis, UV irradiation, chemical mutagenesis, random primer mutagenesis and mutations created by PCR methods.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Cheng, J. and Hass, M. (1992), PCR Methods and Applications, 1:199–201.
Cotton, R. G. H. (1989), Biochem J., 263:1–10.
Dunn et al. (1988), Science, 241:1797–1800
Flavell et al. (1978), Cell, 15:25
Forrester, K., Almoguera, C., Han, K., Grizzie, W. E. and Perucho, M. (1987) Nature, 327:298–303.
Genovese et al. (1989) J. Biol. Chem., 264:9632–9637.
Green, et al. (1983) Cell, 32:681–694
Hayashi, K. (1991) PCR Methods and Applications, 34–35.
Horton, R. M., Hunt, H. D., Ho, S. N., Pullen, J. K., and Pease, L. R. (1989) Gene, 77:61–68.
Innis, M. A., Gelfand, D. H. Sninsky, J. J. and White, T. J. eds (1990) PCR Protocols Academic Press, Inc.
Joslyn, G., (21 other authors), and White, R. (1991) Cell 66:601–613.
Keen, J., Lester, D., Inglehearn, C., Curtis, A., and Bhattacharya, S. (1991) Trends in Genetics, 7:5.
Kinzler, K. W., Nilbert, M. C., Vogelstein, B., Bryan, T. M., Levy, D. B., Smith, K. J., Preisinger, A. C., Hamilton, S. R., Hedge, P., Markham, A., Carlson, M., Joslyn, G., Groden, J., White, R., Miki, Y., Miyoshi, Y., Nishisho, I., and Nakamura, Y. (1991) Science, 251:1366–1370.
Langer, et al. (1981) Proc. Nat. Acad. Sci. USA, 78:6633
Lewin, B. ed. (1983) Genes John Wiley & Sons, New York, N.Y.
Lopez-Galindez, C., Rojas, J. M., Najera, R., Richman, D. D., and Perucho, M. (1991) Proc. Natl. Acad. Sci. USA, 88:4280–4284.
Melton, D. A., Krieg, P. A. Rebagliati, M. R., Maniatis, T., Zinn, K. and M. R. Green (1984) Nucleic Acids Research, 12:7035.
Myers, et al. (1985) Nuc. Acid Res., 13:3111.
Myers, R. M., Larin, Z., and Maniatis, T. (1985) Science, 230:1242–1246.
Myers, R. M. and Maniatis, T. (1986) CSH Symposia on Quantitative Biology L1, 275–284.
Nishisho, I., Nakamure, U., Miyoshi, Y., Miki, Y., Ando, H., Horii, A., Koyama, K., Utsunomiya, J., Baba, S., Hedge, P., Markham, A., Krush, A. J., Petersen, G., Hamilton, S. R., Nilbert, M. C., Levy, D. B., Bryan, T. M., Preisinger, A. C., Smith, K. J., Su, L. K., Kinzler, K. W., and Vogelstein, 7B. (1991) Science, 253:665–669.
Orita, M., Iwahana, J., Kanazawa, H., Hayashi, K., and Sekiya, T. (1989) Proc. Natl. Acad. Sci. USA, 86:2766–2770.
Orkin, et al. (1984) Ann. Rev. Genet., 18:131.
Orkin et al. (1983) J. Clin. Invest., 71:775.
Perucho, M. (1989) Strategies in Molecular Biology, 2(3):37–41.
Pitulle, C., Kleineida, R. G., Sproat, B., and Krupp, G. (1992) Gene, 112:101–105
Raines, R. T. (1991) Structure, Mechanism and Function of Ribonucleases, Proceedings of the Second International Meeting (C. M. Cuchillo, R. de Llorens, M. V. Nogues, and X. Pares, Ed.) 139–143, Universitat Autonoma de Barcelona, Bellaterra, Spain.
Richman, A., and Hayday, A. (1989) Science, 246:494–497.
Sambrook, J., Fritsch, E. F., and Maniatis, T. (1989), Molecular Cloning: A Laboratory Manual (2nd Ed.), Cold Spring Harbor University Press, Cold Spring Harbor, N.Y.
Sarkar, S., Yoon, H. S., and Sommer, S. S. (1992) Nucleic Acids Research, 20(4):871–878.
Shenk et al. (1975) Proc. Natl. Acad. Sci. USA, 72:989.
Solomon, et al. (1979) The Lancet 1:923.
Stoflet et al. (1988) Science, 239:491–494.
Storch et al. (1989) J. Clin. Invest., 83:1894–1902.
Takahashi, T., Nau, M. M., Chiba, I., Birrer, M. J., Rosenberg, R. K., Vinocour, M., Levitt, M., Pass, H., Gazdar, A. F., Minna, J. D. (1989) Science, 27:491–494.
Wallace, et al. (1979) Nucl. Acids Res. 6:3543.
Winter et al. (1985) Proc. Natl. Acad. Sci., 82:7575–7579.
Yandell, D. W., Campbell, T. A., Dayton, S., Peterson, R., Walton, D., Little, J. B., McConkie-Rosell, A., Buckley, E. G., and Dryja, T. P. (1989) New England Journal of Medicine, 321:1689–1695.
U.S. application Ser. No. 07/810,968.
U.S. Pat. No. 4,683,202.
U.S. Pat. No. 4,946,773.

What is claimed is:

1. A method for detecting a base pair mismatch between a nucleic acid sample and a single stranded RNA probe, comprising the steps of:

(a) separately contacting a single stranded RNA probe with a control nucleic acid sample and a test nucleic acid sample, thereby forming a control duplex, which is free from mismatches, and a test duplex;

(b) treating said control duplex and said test duplex with a composition comprising an RNase enzyme at a final concentration of between about 0.1 ng/ml and about 4000 ng/ml in a final salt concentration of between about 3 mM and about 90 mM; and (c) detecting a difference in the products of said RNase treated duplexes;

wherein said difference indicates a base pair mismatch.

2. The method of claim 1, wherein step (c) comprises the steps of:

(a) separating the products of said RNase treated control duplex and said RNase treated test duplex; and (b) comparing the products from said control duplex with the products from said test duplex, wherein a difference in the number or sizes of the products is indicative of the presence of a mismatch in said test duplex.

3. The method of claim 1, wherein said final salt concentration is between about 3 mM and about 50 mM.

4. The method of claim 3, wherein said final salt concentration is between about 3 mM and about 10 mM.

5. The method of claim 1, wherein said salt is NaCl, LiCl, Na-acetate, $MgCl_2$, KCl, $MgSO_4$ or $CaCl_2$.

6. The method of claim 1, wherein said RNase enzyme is at a final concentration of between about 1 ng/ml and about 1000 ng/ml.

7. The method of claim 6, wherein said RNase enzyme is at a final concentration of between about 3 ng/ml and about 100 ng/ml.

8. The method of claim 7, wherein said RNase enzyme is at a final concentration of between about 3 ng/ml and about 10 ng/ml.

9. The method of claim 1, wherein the RNase enzyme composition is selected from the group consisting of RNase A, modified RNase A, RNase B, a mixture of RNase A and RNase B, pancreatic RNase, RNase I, RNase T2, RNase P1, and mixtures thereof.

10. The method of claim 9, wherein said RNase enzyme is RNase A, modified RNase A, a mixture of RNase A and RNase B, RNase I or modified RNase I and said final salt concentration is between about 3 mM and about 10 mM.

11. The method of claim 2, wherein said separating step comprises gel electrophoresis.

12. The method of claim 11, wherein said gel electrophoresis is agarose gel electrophoresis or polyacrylamide gel electrophoresis.

13. The method of claim 1, wherein said single stranded RNA probe is labelled.

14. The method of claim 13, wherein said label is radioactive.

15. The method of claim 1, wherein said single stranded RNA probe is synthesized from a bacteriophage or viral promoter.

16. The method of claim 15, wherein said promoter is an SP6, T7 or T3 promoter.

17. The method of claim 1, wherein said nucleic acid sample comprises DNA or RNA.

18. The method of claim 1, wherein said nucleic acid sample is DNA or RNA prepared using the polymerase chain reaction (PCR).

19. An improved method for conducting an RNase protection assay using a nucleic acid sample and a single stranded RNA probe, wherein the improvement comprises conducting the assay in a reduced salt, low enzyme concentration solution.

20. The method of claim 19, wherein said solution contains a final salt concentration of between about 3 mM and about 90 mM and a final RNase enzyme concentration of between about 0.5 ng/ml and about 4000 ng/ml.

21. The method of claim 20, wherein said solution contains a final salt concentration of between about 3 mM and about 50 mM and a final RNase enzyme concentration of between about 3 ng/ml and about 50 ng/ml.

22. The method of claim 21, wherein said solution contains a final salt concentration of between about 3 mM and about 10 mM and a final RNase enzyme concentration of between about 3 ng/ml and about 10 ng/ml.

23. The method of claim 19, wherein said RNase enzyme is RNase A, modified RNase A, a mixture of RNase A and RNase B, RNase I or modified RNase I.

24. The method of claim 19, wherein said nucleic acid sample is DNA or RNA prepared using the polymerase chain reaction (PCR).

25. A method for detecting a mutation in a nucleic acid sample; comprising:
    (a) obtaining a nucleic acid test sample to be analyzed and a nucleic acid non-mutant control sample;
    (b) separately contacting said non-mutant control sample and said test sample with a single stranded RNA probe, thereby forming a non-mutant control duplex, which is free from mismatches, and a test duplex;
    (c) treating said non-mutant control duplex and said test duplex with a composition comprising an RNase enzyme at a final concentration of between about 0.5 ng/ml and about 4000 ng/ml in a final salt concentration of between about 3 mM and about 90 mM;
    (d) separating the products of said RNase treated non-mutant control duplex and said RNase treated test duplex; and
    (e) comparing the products from said non-mutant control duplex with the products from said test duplex, wherein a difference in the number and/or sizes of the products is indicative of the presence of a mutation in said DNA or RNA test sample.

26. The method of claim 25, wherein said RNase enzyme is RNase A, modified RNase A, a mixture of RNase A and RNase B, RNase I or modified RNase I at a final concentration of between about 3 ng/ml and about 10 ng/ml and said final salt concentration is between about 3 mM and about 10 mM.

27. The method of claim 25, wherein said nucleic acid sample comprises DNA or RNA obtained from somatic cells.

28. The method of claim 25, wherein said nucleic acid sample is DNA or RNA prepared using the polymerase chain reaction (PCR).

29. The method of claim 25, wherein said mutation is a single point mutation.

30. The method of claim 25, wherein said mutation lies within the p53 gene.

31. A method for detecting a base pair mismatch between a nucleic acid sample and a single stranded RNA probe, comprising the steps of:
    (a) separately contacting a single stranded RNA probe with a control nucleic acid sample and a test nucleic acid sample, thereby forming a control duplex, which is free from mismatches, and a test duplex;
    (b) treating said control duplex and said test duplex with a composition comprising an RNase enzyme at a final concentration of between about 0.2 units/ml RNase activity and about 8,000 units/ml RNase activity in a final salt concentration of between about 3 mM and about 90 mM; and
    (c) detecting a difference in the products of said RNase treated duplexes;
wherein said difference indicates a base pair mismatch.

32. The method of claim 31, wherein step (c) comprises the steps of:
    (a) separating the products of said RNase treated control duplex and said RNase treated test duplex; and
    (b) comparing the products from said control duplex with the products from said test duplex, wherein a difference in the number or sizes of the products is indicative of the presence of a mismatch in said test duplex.

33. The method of claim 31, wherein said final salt concentration is between about 3 mM and about 50 mM.

34. The method of claim 33, wherein said final salt concentration is between about 3 mM and about 10 mM.

35. The method of claim 31, wherein said RNase enzyme is at a final concentration of between about 2 units/ml RNase activity and about 2000 units/ml RNase activity.

36. The method of claim 35, wherein said RNase enzyme is at a final concentration of between about 6 units/ml RNase activity and about 200 units/ml RNase activity.

37. The method of claim 36, wherein said RNase enzyme is at a final concentration of between about 6 units/ml RNase activity and about 20 units/ml RNase activity.

38. The reaction mixture comprising a final salt concentration of between about 3 mM and about 90 mM and a final RNase enzyme concentration of between about 1 unit/ml and about 8000 units/ml.

39. The reaction mixture of claim 38, wherein said final salt concentration is between about 3 mM and about 50 mM.

40. The reaction mixture of claim 39, wherein said final salt concentration is between about 3 mM and about 10 mM.

41. The reaction mixture of claim 32, wherein said RNase enzyme is at a final concentration of between about 2 units/ml and about 200 units/ml.

42. The reaction mixture of claim 41, wherein said RNase enzyme is at a final concentration of between about 6 units/ml and about 100 units/ml.

43. The reaction mixture of claim 32, wherein said RNase enzyme is RNase A, modified RNase A, a mixture of RNase A and RNase B, RNase I or modified RNase I at a final concentration of between about 6 units/ml and about 20 units/ml and said final salt concentration is between about 3 mM and about 10 mM.

44. A kit for use in conducting an RNase protection assay comprising a suitably aliquoted reaction mixture of claim 32, or a mixture which, when admixed, diluted or brought into solution, will provide such a reaction mixture; a double stranded control nucleic acid sample; and two single stranded control RNA probes, each complementary to one strand of the control nucleic acid sample.

* * * * *

UNITED STATES PATENT AND TRADEMARK OFFICE
CERTIFICATE OF CORRECTION

PATENT NO.   :   5,589,329
DATED        :   December 31, 1996
INVENTOR(S)  :   Winkler et al.

It is certified that error appears in the above-identified patent and that said Letters Patent is hereby corrected as shown below:

In claim 41, column 28, line 59, delete "32" and insert --38--therefor.

In claim 43, column 28, line 65, delete "32" and insert --38--therefor.

In claim 44, column 29, line 6, delete "32" and insert --38--therefor.

Signed and Sealed this

Twenty-ninth Day of April, 1997

*Attest:*

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,589,329
DATED : December 31, 1996
INVENTOR(S) : Winkler et al.

Page 1 of 1

It is certified that error appears in the above-identified patent and that said Letters Patent is hereby corrected as shown below:

<u>Column 1,</u>
Lines 4-6, please delete "The government may own rights in the present invention pursuant to grant number CA57045 from National Institutes of Health" and insert therefor the following:

-- This invention was made with government support under R43CA57045 awarded by the National Cancer Institute. The government has certain rights in the invention. --

Signed and Sealed this

Twentieth Day of August, 2002

*Attest:*

JAMES E. ROGAN
*Attesting Officer*   *Director of the United States Patent and Trademark Office*